US012642756B2

(12) United States Patent
Fadel et al.

(10) Patent No.: US 12,642,756 B2
(45) Date of Patent: Jun. 2, 2026

(54) LEAVE-ON COMPOSITION

(71) Applicant: Firmenich SA, Satigny (CH)

(72) Inventors: Addi Fadel, Plainsboro, NJ (US); Artem Kirshon, Plainsboro, NJ (US); Gary Womack, Plainsboro, NJ (US)

(73) Assignee: FIRMENICH SA, Satigny (CH)

( * ) Notice: Subject to any disclaimer, the term of this patent is extended or adjusted under 35 U.S.C. 154(b) by 395 days.

(21) Appl. No.: 18/249,717

(22) PCT Filed: Sep. 21, 2021

(86) PCT No.: PCT/EP2021/075888
§ 371 (c)(1),
(2) Date: Apr. 19, 2023

(87) PCT Pub. No.: WO2022/063755
PCT Pub. Date: Mar. 31, 2022

(65) Prior Publication Data

US 2024/0016727 A1 Jan. 18, 2024

Related U.S. Application Data

(60) Provisional application No. 63/083,592, filed on Sep. 25, 2020.

(30) Foreign Application Priority Data

Oct. 16, 2020 (EP) .................................... 20202320

(51) Int. Cl.

| | |
|---|---|
| ***A61K 8/37*** | (2006.01) |
| ***A61K 8/92*** | (2006.01) |
| ***A61Q 5/00*** | (2006.01) |
| ***A61Q 15/00*** | (2006.01) |
| ***A61Q 19/00*** | (2006.01) |

(52) U.S. Cl.
CPC .................. *A61K 8/92* (2013.01); *A61Q 5/00* (2013.01); *A61Q 15/00* (2013.01); *A61Q 19/00* (2013.01); *A61K 2800/77* (2013.01)

(58) Field of Classification Search
None
See application file for complete search history.

(56) References Cited

FOREIGN PATENT DOCUMENTS

WO WO-2020260598 A1 * 12/2020 ........... C11D 3/2093

OTHER PUBLICATIONS

Api A M et al., "RIFM Fragrance Ingredient Safety Assessment, (E,Z)-2,6-nonadien-1-ol acetate, CAS Registry No. 68555-65-7", Food and Chemical Toxicology, vol. 127, pp. S216-S223, (Mar. 11, 2019).

* cited by examiner

*Primary Examiner* — Brian Gulledge

(57) ABSTRACT

The present invention relates to the field of perfumery. More particularly, it concerns a consumer product comprising at least one compound of formula (I) and, optionally, a personal care active base. Moreover, the present invention relates to a method of imparting a long-lasting odor, in particular green odor, to surfaces, such as skin or hair.

19 Claims, 4 Drawing Sheets

LEAVE-ON COMPOSITION

This present application is a U.S. national phase entry under 35 U.S.C. § 371 of PCT Application No. PCT/EP2021/075888, filed Sep. 21, 2021 which claims priority to U.S. Provisional Patent Application No. 63/083,592, filed Sep. 25, 2020, and European Patent Application No. 20202320.6, filed Oct. 16, 2020. The entire contents of these applications are explicitly incorporated herein by this reference.

TECHNICAL FIELD

The present invention relates to the field of perfumery. More particularly, it concerns a consumer product comprising at least one compound of formula (I) and, optionally, a personal care active base. Moreover, the present invention relates to a method of imparting a long-lasting odor, in particular green odor, to surfaces, such as skin or hair.

BACKGROUND OF THE INVENTION

The perfume industry has an interest in compositions or additives which are capable of prolonging or enhancing the perfuming effect of at least one perfuming ingredient for a certain period of time. It is particularly desirable to obtain long-lasting properties for standard perfumery raw materials which are too volatile or have a poor substantivity by themselves, or which are only deposited in a small amount onto the surface of the final application. Furthermore, some of the perfumery ingredients are unstable and need to be protected against slow degradation prior to their use. Long-lasting perfumes are desirable for various applications, as for example fine or functional perfumery or cosmetic preparations.

In order to improve the long lastingness of a perfume, fragrance precursors, also called profragrances or properfumes, have been largely developed and used in the industry. The controlled release of at least one perfumery ingredient from their precursor is triggered by a covalent bond cleavage under mild environmental conditions. Laundry care applications have been particularly keen for these kinds of technologies as many active substances which are particularly suitable for this type of applications are known to lack tenacity on laundry, or do not remain on the laundry when rinsed, with the result that their perfuming effect is experienced only briefly and not very intensely. Profragrances developed for laundry care allow releasing perfumery ingredients slowly during several days. However, other applications such as leave-on applications require perfumes, or perfuming compositions, to be effective within 24 h. Due to this different time scale between both type of applications, most of the fragrance precursors particularly effective for laundry care application have less impact on leave-on applications. So, there is a need to develop a more versatile fragrance precursor performing well in all types of applications.

It has now been surprisingly found that compounds of formula (I) solve the above-mentioned problems and are capable of efficiently releasing (2E,6Z)-nona-2,6-dien-1-ol in all types of applications and, particularly, in leave-on applications.

DESCRIPTION OF THE INVENTION

Figure 1:
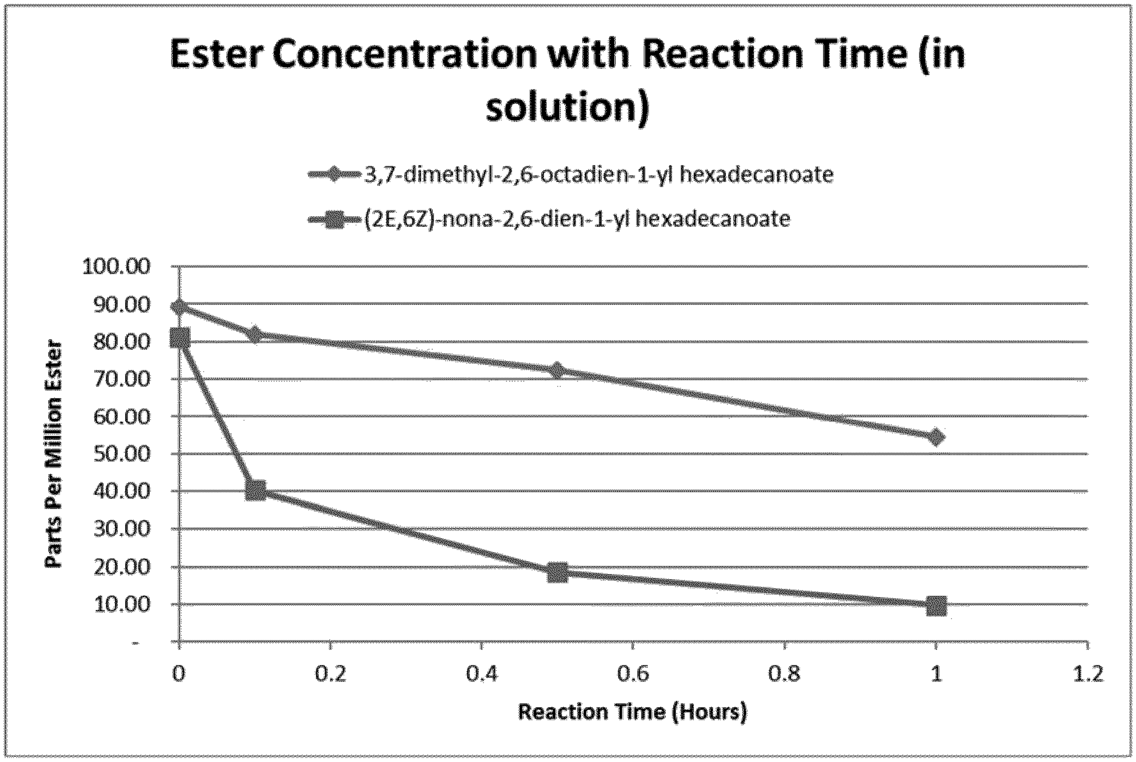
FIG. 1: Analysis of the concentration of 3,7-dimethyl-2,6-octadien-1-yl hexadecanoate and (2E,6Z)-nona-2,6-dien-1-yl hexadecanoate in solution in function of time.

Surprisingly, it has now been discovered that a compound of formula (I) is particularly efficient to release in a controlled manner (2E,6Z)-nona-2,6-dien-1-ol and on a time scale particularly relevant for leave-on applications.

So a first object of the present invention is a perfumed consumer product comprising a) a perfume oil comprising at least one compound of formula (I)

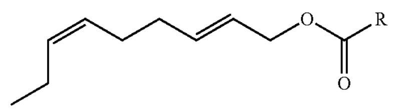

(I)

in the form of any one of its stereoisomers or as a mixture thereof, wherein R represents a linear or branched, saturated or unsaturated $C_{7-24}$ alkyl group;

b) optionally, a personal care active base.

For the sake of clarity, by the expression "any one of its stereoisomers or a mixture thereof", or the similar, it is meant the normal meaning understood by a person skilled in the art, i.e. that the compound of formula (I) can be a pure enantiomer or diastereomer. In other words, the compound of formula (I) may possess several stereocenters, in particular the R group, and each of said stereocenter can have two different stereochemistries (e.g. R or S) or the compound of formula (I) may possess one or more double bonds, in particular the R group, and each of said double bond can be in the form of its E or Z isomer or of a mixture thereof. The compound of formula (I) may even be in the form of a pure enantiomer (if chiral), a pure diastereoisomer (if two or more stereocenters or one or more double bonds) or in the form of a mixture of enantiomers or diastereoisomers. The compound of formula (I) can be in a racemic form or scalemic form. Therefore, the compound of formula (I) can be one stereoisomer or in the form of a composition of matter comprising, or consisting of, various stereoisomers.

According to any embodiments of the invention, R may be a linear, saturated or unsaturated $C_{9-21}$ alkyl group. Particularly, R may be a linear saturated $C_{10-18}$ alkyl group. Particularly, R may be a linear saturated $C_{11-16}$ alkyl group. Particularly, R may be a linear saturated $C_{11}$ alkyl group, a linear saturated $C_{13}$ alkyl group or a linear saturated $C_{15}$ alkyl group.

According to any embodiments of the invention, the compound of formula (I) may be (2E,6Z)-nona-2,6-dien-1-yl hexadecanoate, (2E,6Z)-nona-2,6-dien-1-yl tetradecanoate or (2E,6Z)-nona-2,6-dien-1-yl dodecanoate.

By "perfume oil", it is meant here an ingredient or composition that is a liquid at about According to any one of the above embodiments said perfume oil can be compound of formula (I) alone or a mixture of ingredients currently used in perfumery, such as perfumery carrier, perfumery co-ingredient and/or perfumery adjuvant.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. Solid carriers are of current use in the art and a person skilled in the art knows how to reach the desired effect. However by way of non-limiting examples of solid carriers, one may cite absorbing gums or polymers or inorganic materials, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation techniques.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Other resins are the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate are preferred.

Some of the seminal literature related to the encapsulation of perfumes by polycondensation of amino resins, namely melamine based resins with aldehydes includes articles such as those published by K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinence, which disclose suitable uses of such microcapsules, are represented for example by the article of K. Bruyninckx and M. Dusselier, ACS Sustainable Chemistry & Engineering, 2019, vol. 7, pages 8041-8054.

By "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor. Said perfuming co-ingredient is not of formula (I)

The nature and type of the perfuming co-ingredients present in the composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or *sulphurous* heterocyclic compounds and essential oils, and said perfuming co-ingredients can be of natural or synthetic origin.

In particular one may cite perfuming co-ingredients which are commonly used in perfume formulations, such as:

Aldehydic ingredients: decanal, dodecanal, 2-methyl-undecanal, 10-undecenal, octanal, nonanal and/or nonenal;

Aromatic-herbal ingredients: eucalyptus oil, camphor, eucalyptol, 5-methyltricyclo[6.2.1.0-2,7-]undecan-4-one, 1-methoxy-3-hexanethiol, 2-ethyl-4,4-dimethyl-1,3-oxathiane, 2,2,7/8,9/10-Tetramethylspiro[5.5]undec-8-en-1-one, menthol and/or alpha-pinene;

Balsamic ingredients: coumarin, ethylvanillin and/or vanillin;

Citrus ingredients: dihydromyrcenol, citral, orange oil, linalyl acetate, citronellyl nitrile, orange terpenes, limonene, 1-p-menthen-8-yl acetate and/or 1,4(8)-p-menthadiene;

Floral ingredients: methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino) benzoate, (E)-3-methyl-4-(2,6,6-trimethyl-2-cyclohexen-1-yl)-3-buten-2-one, (1E)-1-(2,6,6-trimethyl-2-cyclohexen-1-yl)-1-penten-3-one, 1-(2,6,6-trimethyl-1,3-cyclohexadien-1-yl)-2-buten-1-one, (2E)-1-(2,6,6-trimethyl-2-cyclohexen-1-yl)-2-buten-1-one, (2E)-1-[2,6,6-trimethyl-3-cyclohexen-1-yl]-2-buten-1-one, (2E)-1-(2,6,6-trimethyl-1-cyclohexen-1-yl)-2-buten-1-one, 2,5-dimethyl-2-indanmethanol, 2,6,6-trimethyl-3-cyclohexene-1-carboxylate, dimethyl-1-cyclohexen-1-yl)propanal, hexyl salicylate, 3,7-dimethyl-1,6-nonadien-3-ol, 3-(4-isopropylphenyl)-2-methylpropanal, verdyl acetate, geraniol, p-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-p-menthanol, propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 8-decen-5-olide, 4-phenyl-2-butanone, isononyle acetate, 4-(1,1-dimethylethyl)-1-cyclohexyl acetate, verdyl isobutyrate and/or mixture of methylionones isomers;

Fruity ingredients: gamma-undecalactone, 2,2,5-trimethyl-5-pentylcyclopentanone, 2-methyl-4-propyl-1,3-oxathiane, 4-decanolide, ethyl 2-methyl-pentanoate, hexyl acetate, ethyl 2-methylbutanoate, gamma-nonalactone, allyl heptanoate, 2-phenoxyethyl isobutyrate, ethyl 2-methyl-1,3-dioxolane-2-acetate, 3-(3,3/1,1-dimethyl-5-indanyl)propanal, diethyl 1,4-cyclohexanedicarboxylate, 3-methyl-2-hexen-1-yl acetate, 1-[3,3-dimethylcyclohexyl]ethyl [3-ethyl-2-oxiranyl]acetate and/or diethyl 1,4-cyclohexane dicarboxylate;

Green ingredients: 2-methyl-3-hexanone (E)-oxime, 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, (Z)-4-cyclopentadecen-1-one, 3-methylcyclopentadecanone, 1-oxa-12-cyclohexadecen-2-one, 1-oxa-13-cyclohexadecen-2-one, (9Z)-9-cycloheptadecen-1-one, 2-{1S)-1-[(1R)-3,3-dimethylcyclohexyl] ethoxy}-2-oxoethyl propionate 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, oxacyclohexadecan-2-one and/or (1S,1'R)-[1-(3',3'-dimethyl-1'-cyclohexyl) ethoxycarbonyl]methyl propanoate;

Woody ingredients: 1-[(1RS,6SR)-2,2,6-trimethylcyclohexyl]-3-hexanol, 3,3-dimethyl-5-[(1R)-2,2,3-trimethyl-3-cyclopenten-1-yl]-4-penten-2-ol, 3,4'-dimethylspiro[oxirane-2,9'-tricyclo[6.2.1.$0^{2,7}$]undec[4]ene, (1-ethoxyethoxy)cyclododecane, 2,2,9,11-tetramethylspiro[5.5]undec-8-en-1-yl acetate, 1-(octahydro-2,3,8,8-tetramethyl-2-naphtalenyl)-1-ethanone, patchouli oil, terpenes fractions of patchouli oil, Clearwood®, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1,3-benzodioxol-5-yl)-2-methylpropanal, 7-methyl-2H-1,5-benzodioxepin-3(4H)-one, 2,5,5-trimethyl-1,2,3,4,4a,5,6,7-octahydro-2-naphthalenol, 1-phenylvinyl acetate, 6-methyl-7-oxa-1-thia-4-azaspiro[4.4]nonan and/or 3-(3-isopropyl-1-phenyl)butanal.

The invention's perfumed consumer product may further comprise other perfuming co-ingredients which are listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds also known as properfume or profragrance. Non-limiting examples of suitable properfume may include 4-(dodecylthio)-4-(2,6,6-trimethyl-2-cyclohexen-1-yl)-2-butanone, 4-(dodecylthio)-4-(2,6,6-trimethyl-1-cyclohexen-1-yl)-2-butanone, 3-(dodecylthio)-1-(2,6,6-trimethyl-3-cyclohexen-1-yl)-1-butanone, 2-(dodecylthio)octan-4-one, 2-phenylethyl oxo(phenyl)acetate, 3,7-dimethylocta-2,6-dien-1-yl oxo(phenyl)acetate, (Z)-hex-3-en-1-yl oxo(phenyl)acetate, 3,7-dimethyl-2,6-octadien-1-yl hexadecanoate, bis(3,7-dimethylocta-2,6-dien-1-yl) succinate, (2-((2-methylundec-1-en-1-yl)oxy)ethyl)benzene, 1-methoxy-4-(3-methyl-4-phenethoxy but-3-en-1-yl)benzene, (3-methyl-4-phenethoxybut-3-en-1-yl)benzene, 1-(((Z)-hex-3-en-1-yl)oxy)-2-methylundec-1-ene, (2-((2-methylundec-1-en-1-yl)oxy)ethoxy)benzene, 2-methyl-1-(octan-3-yloxy)undec-1-ene, 1-methoxy-4-(1-phenethoxyprop-1-en-2-yl)benzene, 1-methyl-4-(1-phenethoxy prop-1-en-2-yl)benzene, 2-(1-phenethoxy prop-1-en-2-yl)naphthalene, (2-phenethoxyvinyl)benzene, 2-(1-((3,7-dimethyloct-6-en-1-yl)oxy)prop-1-en-2-yl)naphthalene, (2-((2-pentylcyclopentylidene)methoxy)ethyl)benzene, (2-((2-heptylcyclopentylidene)methoxy)ethyl)benzene, 1-isopropyl-4-methyl-2-((2-pentylcyclopentydene)methoxy)benzene, 2-methoxy-1-((2-pentylcyclopentydene)methoxy)-4-propylbenzene, 3-methoxy-4-((2-methoxy-2-phenylvinyl)oxy)benzaldehyde, 4-((2-(hexyloxy)-2-phenylvinyl)oxy)-3-methoxybenzaldehyde or a mixture thereof.

By "perfumery adjuvant", it is meant here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungal or anti irritant agents), abrasives, skin cooling agents, fixatives, insect repellants, ointments, vitamins and mixtures thereof.

It is understood that a person skilled in the art is perfectly able to design optimal perfume oil formulations for the desired effect by admixing the above-mentioned components of the perfume oil, simply by applying the standard knowledge of the art as well as by trial and error methodologies.

A perfume oil consisting of at least one compound of formula (I) and at least one perfumery carrier consists of a particular embodiment of the invention as well as a perfume oil comprising at least one compound of formula (I), at least one perfumery carrier, at least one perfumery co-ingredient, and optionally at least one perfumery adjuvant.

According to a particular embodiment, the perfume oil mentioned above, comprise more than one compound of formula (I) and enable the perfumer to prepare accords or perfumes possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of formula (I) would be involved as a starting, intermediate or end-product could not be considered as a perfuming composition according to the invention as far as said mixture does not provide the compound of formula (I) in a suitable form for perfumery. Thus, unpurified reaction mixtures are generally excluded from the present invention unless otherwise specified.

For the sake of clarity, "perfumed consumer product" is meant to designate a consumer product which is expected to deliver among different benefits a pleasant perfuming effect to the surface or space to which it is applied (e.g. skin, hair, textile, paper or home surface) or in the air (air-freshener, deodorizer etc). In other words, a perfumed consumer product according to the invention is a manufactured product which comprises a functional formulation also referred to as "base", together with benefit agents, corresponding to the desired consumer product, and an olfactive effective amount of at least one compound of formula (I). For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer products include a perfume, such as a fine perfume, a splash or eau de parfum, a cologne or a shave or after-shave lotion; a body-care product, such as a hair care product (e.g. a shampoo, a coloring preparation or a hair spray, a color-care product, a hair shaping product), a dental care product, a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products).

According to a particular embodiment, the perfumed consumer product is a leave-on consumer product.

By "leave-on consumer product" or similar, it is meant a consumer product is intended to stay in prolonged contact with the skin, the hair or the mucous membranes, by contrast to rinse-off consumer product.

Non-limiting examples of suitable perfumed leave-on consumer product include:

a perfume, such as a fine perfume, a splash, an eau de toilette, an eau de parfum, a cologne or a shave or after-shave lotion;

a hair care product, such as a hair cream, a hair oil, a hair styling product (such as a spray, mousse or gel), a leave-on hair conditioner, a hair tonic;

a skin care product, such as a face cream, a face lotion, a shaving product (such as a foam, cream, gel or oil), a body and/or hand product (such as a lotion, cream, gel or oil), a skin firming product, a depilatory, a talcum powder, a foot care cream or lotion, a baby wipe, a cleansing wipe, a moisturizer wipe, a sun-protection product (such as a spray, lotion, cream or oil), an after-sun lotion, or a self-tanning product;

a body deodorant or antiperspirant product, such as a body deodorant spray, a roll-on deodorant, a deodorant stick, a deodorant cream, an antiperspirant spray, an antiperspirant stick, a roll-on antiperspirant liquid, an antiperspirant stick, or an antiperspirant cream;

By personal care active base, it is meant here an ingredient capable of imparting a benefit associated with the personal consumer product such as texture, moisturizing agent, etc. . . . . The personal care active base in which the compound of formula (I) can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

According to any embodiments of the invention, the perfumed consumer product may be in the form of a perfume. Particularly, the perfumed consumer product may be in the form of a fine perfume, a splash, an eau de toilette, an eau de parfum, a cologne or a shave or after-shave lotion. The perfumed consumer product may be in the form of a fine perfume, an eau de toilette, an eau de parfum, a cologne or a shave or after-shave lotion comprising a) 0.0001% to 5% w/w, preferably 0.01% to 1% w/w, of at least one compound of formula (I)

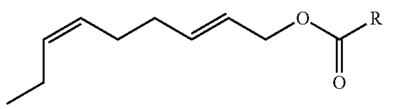

(I)

in the form of any one of its stereoisomers or as a mixture thereof, wherein R represents a linear or branched, saturated or unsaturated $C_{7-24}$ alkyl group;

b) 20% to 90% w/w, preferably 40% to 90% w/w, of a perfumery carrier wherein the perfumery carrier is ethanol;

c) 0.3% to 30% w/w, preferably 1% to 15% w/w, of at least one perfumery co-ingredient; and d) optionally at least one perfumery adjuvant;

the percentage being relative to the total weight of the perfumed consumer product.

According to any embodiments of the invention, the perfumed consumer product in the form of a perfume may further comprise a modulator, also called fixative.

By "modulator", it is understood here an agent having the capacity to affect the manner in which the odour, and in particular the evaporation rate and intensity, of the compositions incorporating said modulator can be perceived by an observer or user thereof, over time, as compared to the same perception in the absence of the modulator. In particular, the modulator allows prolonging the time during which their fragrance is perceived. Non-limiting examples of suitable modulators may include methyl glucoside polyol; ethyl glucoside polyol; propyl glucoside polyol; isocetyl alcohol; PPG-3 myristyl ether; neopentyl glycol diethylhexanoate; sucrose laurate; sucrose dilaurate, sucrose myristate, sucrose palmitate, sucrose stearate, sucrose distearate, sucrose tristearate, hyaluronic acid disaccharide sodium salt, sodium hyaluronate, propylene glycol propyl ether; dicetyl ether; polyglycerin-4 ethers; isoceteth-5; isoceteth-7, isoceteth-10; isoceteth-12; isoceteth-15; isoceteth-20; isoceteth-25; isoceteth-30; disodium lauroamphodipropionate; hexaethylene glycol monododecyl ether; and their mixtures; neopentyl glycol diisononanoate; cetearyl ethylhexanoate; panthenol ethyl ether, DL-panthenol, N-hexadecyl n-nonanoate, noctadecyl n-nonanoate, a profragrance, cyclodextrin, an encapsulation, and a combination thereof. At most 20% by weight, based on the total weight of the perfuming composition, of the modulator may be incorporated into the perfumed consumer product.

According to any embodiments of the invention, when the perfumed consumer product is in the form of a body spray or body splash, the perfumery carrier may be water, ethanol or a mixture thereof. The body spray or body splash may be in the form of an aerosol or a natural spray. The perfumed consumer product in the form of a perfume body spray or body splash may further comprise humectants, such as for example, glycerin, propylene glycol, butylene glycol polyethylene glycol or other suitable glycols type compounds; emollients, such as for example, silicones, esters, caprylic capric triglycerides; actives (soothing, antiaging, moisturizing, UV filters such as methoxycinnamate or benzophenone, botanical extracts such as aloe vera or rose extracts); cooling compounds; polymers, such as for example, carbomers, acrylates, polyvinylpyrrolidone; surfactants such as for example quaternium, solubilizers such as for example, nonionic surfactants with high HLB, mainly PEG-40 or 60 hydrogenated castor oil, polysorbate; antibacterial actives, such as for example, triethyl citrate, ethylhexylglycerin or ethanal, or propellants such as compressed air.

According to any embodiments of the invention, the perfumed consumer product may be in the form of a skin care consumer product. Particularly, the perfumed consumer product may be in the form of a face cream, a face lotion, a shaving product, a body and/or hand product, a skin firming product, a depilatory, a talcum powder, a foot care cream or lotion, a baby wipe, a cleansing wipe, a moisturizer wipe, a sun-protection product, an after-sun lotion, or a self-tanning product. The perfumed consumer product may be in the form of skin care product comprising at least one skin care active base. Non-limiting examples of suitable skin care active base may include dermatologically-acceptable carriers, stabilizing agents, moisturizing agents, thickening agents, gelling agents, preservatives, anti-inflammatory agents or anti-acne agents.

The dermatologically-acceptable carriers used can be water or aqueous solutions; oils, such as triglycerides of capric or of caprylic acid, or castor oil; fats, waxes and other natural and synthetic fatty materials, preferably esters of fatty acids with alcohols of low C number, e.g. with isopropanol, propylene glycol or glycerol, or esters of fatty alcohols with alkanoic acids of low C number or with fatty acids; alcohols of low C number, and also their ethers, preferably ethanol, isopropanol, glycerol, ethylene glycol, ethylene glycol monoethyl or monobutyl ether, propylene glycol monomethyl, monoethyl or monobutyl ether, diethylene glycol monomethyl or monoethyl ether and analogous products. In some cases, mixtures of the abovementioned solvents are used. In the case of alcoholic solvents, water can be a further constituent.

Some specific examples of dermatologically-acceptable carriers suitable for application with the invention include water, olive oil, peanut oil, sesame oil, sunflower oil, safflower oil, arachis oil, coconut oil, liquid paraffin, polyethyleneglycol, ethanol, propanol, isopropanol, glycerol, fatty alcohols, triglycerides, polyvinyl alcohol, partially hydrolysed poly vinyl acetate. Other suitable carriers would be appreciated by one having ordinary skill in the art.

The carrier component may comprise oils, which in one embodiment are present in the oil phase of an emulsion, selected from hydrocarbon oils such as paraffin or mineral oils; b) waxes such as beeswax or paraffin wax; c) natural oils such as sunflower oil, apricot kernel oil, shea butter or jojoba oil; d) silicone oils such as dimethicone, cyclomethicone or cetyldimethicone; e) fatty acid esters such as isopropyl palmitate, isopropyl myristate, dioctylmaleate, glyceryl oleate and cetostearyl isononanoate; f) fatty alcohols such as cetyl alcohol or stearyl alcohol and mixtures thereof (e.g. cetearyl alcohol); g) polypropylene glycol or polyethylene glycol ethers, e.g. PPG-14 butyl ether; or h) mixtures thereof, for example, the blend of waxes available commercially under the trade name Cutina (Cognis).

The carrier can be in the form of a hydroalcoholic system (e.g. liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semi-solids (such as gels and sticks); and aqueous based mousse systems. Non-limiting examples of the topical carrier systems useful in the present invention are described in the following four references, all of which are incorporated herein by reference in their entirety: "Sun Products Formulary", Cosmetics & Toiletries, Vol. 105, pp.

Various embodiments of the skin care active base of the invention may include a stabilizing agent. The stabilizing agent may be an antioxidant selected from the group consisting of amino acids (e.g. glycine, histidine, tyrosine, tryptophan) and their derivatives, imidazoles (e.g. urocanic acid) and their derivatives, peptides such as D,L-carnosine, D-carnosine, L-carnosine and their derivatives (e.g. anserine), carotenoids, carotenes (e.g. α-carotene, β-carotene, lycopene) and their derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulphoximine compounds (e.g. buthionine sulphoximines, homocysteine sulphoximine, buthionine sulphones, penta-, hexa- or heptathioninesulphoxime) in very low tolerable doses (e.g. pmol to .mu.mol/kg), further (metal) chelators (e.g. .alpha.-hydroxy fatty acids, palmitic acid, phytic acid, lactoferrin), alpha.-hydroxy acids (e.g. citric acid, lactic acid, malic acid), humic acid, bile acid, bile extracts, bilirubin, biliverdin, EDTA, EGTA and their derivatives, unsaturated fatty acids and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg-ascorbyl phosphate, ascorbyl acetate), tocopherols and derivatives (e.g. vitamin E acetate), vitamin A and derivatives (vitamin A palmitate) and coniferyl benzoate from benzoin, rustic acid and its derivatives, ferulic acid and its derivatives, butyl hydroxytoluene, butylhydroxyanisole, nordihydroguaiaretic acid, trihydroxybutyrophenone, uric acid and its derivatives, mannose and its derivatives, zinc and its derivatives (e.g. ZnO, $ZnSO_4$), selenium and its derivatives (e.g. selenomethionine), stilbenes and their derivatives (e.g. stilbene oxide, trans-stilbene oxide) and the derivatives suitable according to the invention (salts, esters, ethers, sugars, nucleotides, nucleosides, peptides and lipids) of these said active compounds. The stabilizing agent may be present at a concentration of from 0.2-3.0%.

The skin care active base according to the invention may comprise one or more moisturizing agents, i.e. ingredients intended to increase the water content of the top layers of the skin. Examples of such ingredients are emollients, such as squalane, glycerin, 1,3-butylene glycol, propylene glycol, urea, panthenol, a-hydroxy acids such as lactic acid, hydrolysed proteins, hyaluronic acid, pyrrolidone carbonic acid, as well as naturally-occurring materials such as aloe barbadensis. Other suitable ingredients include glycerol quat, glycerol and hydroxyethyl urea and include the Stratys-3 system sold by the company Unilever or those sold under the name Sheer Infusion. The moisturising agents will generally be water-soluble moisturising agents.

The skin care active base of the present invention can also include a thickening agent. Suitable thickening agents include cellulose and derivatives thereof such as carboxymethylcellulose hydroxyethylcellulose, cellulose acetate propionate carboxylate, hydroxyethylcellulose, hydroxyethylmethylcellulose, hydroxypropylcellulose, hydroxypropyl methylcellulose, methyl hydroxyethylcellulose, microcrystalline cellulose, sodium cellulose sulfate, and mixtures thereof. Further suitable thickening agents include alkyl substituted celluloses. In these polymers a proportion of the hydroxy groups of the cellulose polymer are hydroyxalkylated (preferably hydroxyethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Examples of alkyl groups useful for modifying the hydroxyalkyl cellulose include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof.

Other thickening agents suitable for use with the skin care consumer products of the invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, nano gum, potassium alginate, potassium carrageenan, propylene glycol alginate, sclerotium gum, sodium carboxymethyl dextran, sodium carrageenan, tragacanth gum, xanthan gum, and mixtures thereof.

Gels provided according to the invention may be aqueous or non-aqueous. Aqueous gels are preferred. The gel will contain a gelling agent in order to give sufficient viscosity to the gel. A particularly suitable gelling agent is a copolymer of acryloyl dimethyl tauric acid (or a salt thereof), especially a copolymer of that monomer with another vinylic monomer. The salt may be a salt of a Group I alkali metal, but is more preferably an ammonium salt. Examples of suitable copolymer gelling agents are ammonium acryloyl dimethyl taurate/vinyl pyrrolidone copolymer, ammonium acryloyl dimethyl taurate/Beheneth-25 methacrylate copolymer, ammonium acryloyldimethyltaurate/vinyl formamide copolymer. These materials are available from Clariant GmbH in the range of products under the trade name Aristoflex.

Preferred aqueous systems comprise water in an amount of at least 40% w/w, more preferably at least 50% w/wt, most preferably at least 60% w/w. Some compositions may contain at least 70% or even at least 75% w/w. The upper limit of water will depend on the amounts of other ingredients incorporated in the composition so that the water may form the remainder of the composition up to 100% w/w of the composition. A typical maximum value is less than 90% w/w, for example less than 85% or 80% w/w.

Skin-care active base according to the invention may further include preservatives. Suitable preservatives include, but are not limited to, $C_1$-$C_3$ alkyl parabens and phenoxyethanol, calcium propionate, sodium nitrate, sodium nitrite, sulfites (sulfur dioxide, sodium bisulfate, potassium hydrogen sulfite, etc.) and disodium EDTA. Preservatives are typically present in an amount ranging from about 0.5% to about 2.0% by weight percent, based on the total weight of skin care consumer product.

In one embodiment of the invention the skin care active base may include an anti-inflammatory agent. Examples of anti-inflammatory agents, include, but are not limited to, non-steroidal and steroidal anti-inflammatory agents such as corticosteroids such as hydrocortisone, hydroxyltriamcinolone, alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene, (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluorometha-lone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, and triamcinolone, and combinations thereof. Examples of non-steroidal anti-inflammatory agents include but not limited to COX inhibitors, LOX inhibitors, and p38 kinase inhibitors, immunosuppresant agents such as cyclosporin, and cytokine synthesis inhibitors. Other natural antiinflammatories include, but are not limited to, extracts of feverfew, soy, or oats, beta-glucan, and totarol.

In a further embodiment of the invention the skin care active base may comprise one or more anti-acne agents. Preferably, the further anti-acne agent is selected from desquamators, keratolytics, comedolytics, non-comedolytics and exfoliants. Desquamators, keratolytics, comedolytics and exfoliants aid in the penetration of the active into the skin, and compounds which are capable of serving one or more of these functions are well known in the art. A compound may have one or more of these properties, for example a desquamator may also act as a keratolytic.

According to any embodiments of the invention, the perfumed consumer product may be in the form of a deodorant or antiperspirant product.

As used herein, the term "antiperspirant or deodorant product" refers to the normal meaning in the art; i.e. a composition applied on skin allowing to reduce or prevent body odour.

Particularly, the perfumed consumer product may be in is in the form of a body deodorant spray, a roll-on deodorant, a deodorant stick, a deodorant cream, an antiperspirant spray, an antiperspirant stick, a roll-on antiperspirant liquid, an antiperspirant stick, or an antiperspirant cream. The perfumed consumer product may be in is in the form of a deodorant or antiperspirant product comprising at least one deodorant or antiperspirant active base. Non-limiting examples of suitable deodorant or antiperspirant active base may include emollients, solubilizers, deodorant actives, antioxidants, preservatives, carriers, odour entrappers, propellants, primary structurants, antiperspirant actives, additional chassis ingredients, volatile silicone solvents, gellants, buffering agent and residue masking materials. A person skilled in the art is able to select them on the basis of its general knowledge and according to intended form of the deodorant or antiperspirant composition.

The deodorant or antiperspirant may be in the form of wax-based sticks, soap-based sticks, compressed powder sticks, roll-on suspensions or solutions, emulsions, gels, creams, squeeze sprays, pump sprays, aerosols, and the like. Each product form may contain its own selection of additional deodorant or antiperspirant active base, some essential and some optional.

For example, by way of illustration, a roll-on deodorant or antiperspirant product may comprise water, emollient, solubilizer, deodorant or antiperspirant actives, antioxidants, preservatives, or combinations thereof; a clear gel product or antiperspirant product may comprise water, emollient, solubilizer, deodorant or antiperspirant actives, antioxidants, preservatives, ethanol, or combinations thereof; a body spray may contain a carrier, deodorant or antiperspirant actives, odour entrappers, propellant, or combinations thereof; an invisible solid deodorant or antiperspirant product may contain a primary structurant, deodorant or antiperspirant actives, and additional chassis ingredient(s); a soft solid deodorant or antiperspirant product may comprise volatile silicone, deodorant or antiperspirant actives, gellant, residue masking material, or combinations thereof; an aerosol deodorant or antiperspirant product may comprise a carrier, a propellant, or a combination thereof.

Emollients suitable for deodorant or antiperspirant products include, but are not limited to, propylene glycol, polypropylene glycol (like dipropylene glycol, tripropylene glycol, etc.), diethylene glycol, triethylene glycol, neopentyl glycol diheptanoate, PEG-4, PEG-8, 1,2-pentanediol, 1,2-hexanediol, hexylene glycol, glycerin, $C_2$ to $C_{20}$ monohydric alcohols, $C_2$ to $C_{40}$ dihydric or polyhydric alcohols, alkyl ethers of polyhydric and monohydric alcohols, dicaprylyl carbonate, dicaprylyl ether, diethylhexylcyclohexane, dibutyl adipate, volatile silicone emollients such as cyclopentasiloxane, nonvolatile silicone emollients such as dimethicone, mineral oils, polydecenes, petrolatum, and combinations thereof. One example of a suitable emollient comprises PPG-15 stearyl ether. Other examples of suitable emollients include dipropylene glycol and propylene glycol.

Suitable deodorant actives can include any topical material that is known or otherwise effective in preventing or eliminating malodour, including malodour associated with sweat and/or perspiration. Suitable deodorant actives may be selected from the group consisting of antimicrobial agents (e.g., bacteriocides, fungicides), malodour-absorbing material, and combinations thereof.

Antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

Suitable odour entrappers for use herein include, for example, solubilized, water-soluble, uncomplexed cyclodextrin. As used herein, the term "cyclodextrin" includes any of the known cyclodextrins such as unsubstituted cyclodextrins containing from six to twelve glucose units, including alpha-cyclodextrin, beta-cyclodextrin, gamma-cyclodextrin and/or their derivatives and/or mixtures thereof.

A suitable solubilizer can be, for example, a surfactant, such as a no-foaming or low-foaming surfactant. Suitable surfactants are nonionic surfactants, cationic surfactants, amphoteric surfactants, zwitterionic surfactants, and mixtures thereof. Suitable solubilizers include, for example, polyethylene glycol ether of Cetearyl Alcohol, hydrogenated castor oil such as polyoxyethylene hydrogenated castor oil, polyoxyethylene 2 stearyl ether, polyoxyethylene 20 stearyl ether, and combinations thereof.

Suitable preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof.

Non-limiting examples of commercially available preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathan® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-(1,3-bis(hydroxymethyl)2,5-dioxo-4-imidazolidinyll-N, N'-bis(hydroxy-methyl) urea, commonly known as diazolidinyl urea, available under the trade name Germall® II from Sutton Laboratories, Inc.; N,N"-methylenebis IN'-[1-(hydroxymethyl)-2,5-dioxo-4-imidazolidinyllurea], commonly known as imidazolidinyl urea, available, e.g., under the trade name Abiol® from 3V-Sigma, Unicide U-13® from Induchem, German 115® from Sutton Laboratories, Inc.; polymethoxy bicyclic oxazolidine, available under the trade name Nuosept® C from Hills America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative can range from about 0.0001% to about 0.5%, alternatively from about 0.0002% to about 0.2%, alternatively from about 0.0003% to about %, by weight of the composition.

Suitable carriers can include, water, alcohol, or combinations thereof. Useful alcohols include $C_1$-$C_3$ alcohols. In some aspects, the alcohol is ethanol.

Some examples of propellants include compressed air, nitrogen, inert gases, carbon dioxide, and mixtures thereof. Propellants may also include gaseous hydrocarbons like propane, n-butane, isobutene, cyclopropane, and mixtures thereof e.g. A-46 (a mixture of isobutane, butane and propane), A-31 (isobutane), A-17 (n-butane), A-108 (propane), AP70 (a mixture of propane, isobutane and nbutane), AP40 (a mixture of propane, isobutene and n-butane), AP30 (a mixture of propane, isobutane and n-butane). Some non-limiting examples of propellants include 1,1-difluoroethane, 1,1,1,2,2-pentafluoroethane, 1,1,1,2-tetrafluoroethane, 1,1, 1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof.

The term "primary structurant" as used herein means any material known or otherwise effective in providing suspending, gelling, viscosifying, solidifying, and/or thickening properties to the composition or which otherwise provide structure to the final product form. These primary structurants include gelling agents, and polymeric or non-polymeric or inorganic thickening or viscosifying agents. Such materials will typically be solids under ambient conditions and include organic solids, crystalline or other gellants, inorganic particulates such as clays or silicas, or combinations thereof. Non-limiting examples of suitable primary structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fischer-Tropsch waxes, and microcrystalline wax; polyethylenes with molecular weight of 200 to 1000 daltons; solid triglycerides; behenyl alcohol, or combinations thereof.

Antiperspirant actives may include astringent metallic salts, especially inorganic and organic salts of aluminum, zirconium and zinc, as well as mixtures thereof. Even more specifically, antiperspirant actives may be selected from the group consisting of aluminum chloride, aluminum chlorohydrate, aluminum chlorohydrex, aluminum chlorohydrex PG, aluminum chlorohydrex PEG, aluminum dichlorohydrate, aluminum dichlorohydrex PG, aluminum dichlorohydrex PEG, aluminum sesquichlorohydrate, aluminum sesquichlorohydrex PG, aluminum sesquichlorohydrex PEG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY and aluminum zirconium trichlorohydrate GLY.

Chassis ingredients may be an additional structurant such as stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; and solid triglycerides; behenyl alcohol, or combinations thereof; non-volatile organic fluids such as mineral oil, PPG-14 butyl ether, isopropyl myristate, petrolatum, butyl stearate, cetyl octanoate, butyl myristate, myristyl myristate, C12-15 alkylbenzoate (e.g., Finsolv™), octyldodecanol, isostearyl isostearate, octododecyl benzoate, isostearyl lactate, isostearyl palmitate or isobutyl stearate; clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof.

Volatile silicone solvents suitable for use in the antiperspirant compositions include, but are not limited to, solvent such as Cyclomethicone D-5; GE 7207 and GE 7158 (commercially available from General Electric Co.); Dow Corning 344; Dow Corning 345; Dow Corning 200; and DC1184 (commercially available from Dow Corning Corp.); and SWS-03314 (commercially available from SWS Silicones).

The gellant material may comprise saturated or unsaturated, substituted or unsubstituted, fatty alcohols or mixtures of fatty alcohols having from about 20 to about 60 carbons atoms, alternatively from about 20 to about 40 carbon atoms.

In some embodiments, the gallant materials comprise combinations of the fatty alcohols. In some embodiments, the fatty alcohol gellants are may be saturated, unsubstituted monohydric alcohols or combinations thereof, which have a melting point of at less than about 110° C., alternatively from about 60° to about 110° C., alternatively between about 100° C. and 110° C.

Specific examples of fatty alcohol gellants for use in the antiperspirant products that are commercially available include, but are not limited to, Unilin® 425, Unilin® 350, Unilin® 550 and Unilin® 700 (supplied by Petrolite).

A suitable buffering agent may be alkaline, acidic or neutral. The buffer may be used in the composition or product for maintaining the desired pH. Suitable buffering agents include, for example, hydrochloric acid, sodium hydroxide, potassium hydroxide, and combinations thereof.

Non-limiting examples of suitable residue masking materials for use in the antiperspirant products include butyl stearate, diisopropyl adipate, petrolatum, nonvolatile silicones, octyldodecanol, phenyl trimethicone, isopropyl myristate, $C_{12-15}$ ethanol benzoates and PPG-14 Butyl Ether.

The deodorant or antiperspirant products disclosed herein may comprise other optional ingredients such as emulsifiers, distributing agents, antimicrobials, pharmaceutical or other topical actives, surfactants, and the like.

The nature, amount and type of ingredients does not warrant a more detailed description here, which in any case would not be exhaustive, the skilled person being able to select them on the basis of its general knowledge and according to intended form.

In some aspects, the composition comprises less than 95 wt % of water, relative to the total weight of the composition. In some aspects, the composition comprises less than wt % of water, relative to the total weight of the composition. In some aspects, the composition comprises less than 85 wt % of water, relative to the total weight of the composition. In some aspects, the composition comprises less than 80 wt % of water, relative to the total weight of the composition. In some aspects, the composition comprises less than wt % of water, relative to the total weight of the composition. In some aspects, the composition comprises less than 70 wt % of water, relative to the total weight of the composition. In some aspects, the composition comprises less than 65 wt % of water, relative to the total weight of the composition. In some aspects, the composition comprises less than wt % of water, relative to the total weight of the composition. In some aspects, the composition comprises less than 55 wt % of water, relative to the total weight of the composition. In some aspects, the composition comprises less than 50 wt %, or less than 40 wt %, or less than 30 wt %, or less than 20 wt %, or less than 10 wt % of water, relative to the total weight of the deodorant or antiperspirant composition. In some aspects, the composition is water-free.

According to any embodiments of the invention, the perfumed consumer product may be in the form of a hair care consumer product. Particularly, the perfumed consumer product may be in is in the form of hair cream, a hair oil, a hair styling product (such as a spray, mousse or gel), a leave-on hair conditioner, a hair tonic. The perfumed consumer product may be in is in the form of hair care product comprising at least one hair care active base.

Suitable hair care active may be selected from the group consisting of humectant such as water; disinfecting agent such as alcohol, e.g. denaturated alcohol or isopropyl alcohol; fragrance; fragrance solubilizer, such as PEG-40 hydrogenated Castor Oil, hydrogenated ethoxylated castor oil (also called Cremophore® RH60, origin BASF), polyoxyethylene (20) sorbitan monolaurate, mixture of naturally derived surfactant (also called Symbio® Solv Clear plus, origin: Evonik), mixture of Polyglyceryl-6 Caprylate and polyglyceryl-4 Caprate (also called Tego® Solve 90, origin: Evonik) and/or mixture of polyglyceryl-4 laurate/sebacate and polyglyceryl-6 caprylate/caprate and water (also called Natragem™ S140 NP-LQ, origin: Croda); moisturin agent such as 2,4-dihydroxy-N-(3-hydroxypropyl)-3,3-dimethylbutanamide, glycerin, aloe vere, avocado oil, jojoba oil, sweet almond oil and/or castor oil; cooling agent such as menthol, menthone glycerin acetal, menthyl lactate and/or N-(1H-pyrazol-5-yl)-N-(thiophen-2-ylmethyl)-2-(p-tolyloxy)acetamide; activator oh hair growth such as caffein, cocktail of zinc, copper, silicones, and keratin amino acids, 6-piperidin-1-ylpyrimidine-2,4-diamine 3-oxide and/or pyridine-3-carboxamide; anti-dandruff such as Zinc PCA and/or pyridine-3-carboxamide; acidic agent such as citric acid; antioxidant such as vitamin E, tocopheryl acetate, tocopherol, dioleyl tocopheryl methylsilanol and/or potassium ascorbyl tocopheryl phosphate; and/or conditioning agent such retinyl acetal, retinol and/or retinyl palmitate.

Some of the above-mentioned perfumed consumer products may represent an aggressive medium for the compound of formula (I), so that it may be necessary to protect the latter from premature decomposition, for example by encapsulation. So, according to any embodiments of the invention, the perfume oil may be completely or partly encapsulated in a microcapsule, particularly in a core-shell microcapsule wherein the perfume oil comprising at least one compound of formula (I) is contained in the core surrounded by the shell. In one embodiment, the shell of the microcapsule protects the perfume oil comprising at least one compound of formula (I) from the environment. The shell is made of material which is able to release the perfume oil comprising at least one compound of formula (I). In one embodiment, the shell is made of material which is able to release the perfume oil comprising at least one compound of formula (I) upon breakage of the shell and/or by diffusion through the shell. A person skilled in the art is well aware of processes to prepare said microcapsules.

The nature of the shell can vary. According to a particular embodiment, the shell of the microcapsule comprises a material selected from the group consisting of polyurea, polyurethane, polyamide, polyester, poly(meth)acrylate (i.e. polyacrylate and/or polymethacrylate), polysiloxane, polycarbonate, polysulfonamide, polymers of urea and formaldehyde, melamine and formaldehyde, melamine and urea, or melamine and glyoxal and mixtures thereof. The shell can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to a particular embodiment, the core-shell microcapsule(s) can be prepared by using different encapsulation methods.

In a preferred embodiment, the shell of the microcapsules may be, each independently, selected from the group of aminoplast, polyamide, polyester, polyurea and polyurethane shells and mixtures thereof.

In a particular embodiment, the shell of the microcapsules comprises an aminoplast copolymer, such as melamine-formaldehyde or urea-formaldehyde or cross-linked melamine formaldehyde or melamine glyoxal.

In a particular embodiment, the shell of the microcapsules is polyurea-based made from, for example but not limited to isocyanate-based monomers and amine-containing crosslinkers such as guanidine carbonate and/or guanazole. Certain polyurea microcapsules comprise a polyurea wall which is the reaction product of the polymerisation between at least one polyisocyanate comprising at least two isocyanate functional groups and at least one reactant selected from the group consisting of an amine (for example a water-soluble guanidine salt and guanidine); a colloidal stabilizer or emulsifier; and an encapsulated perfume. However, the use of an amine can be omitted.

In a particular embodiment, the colloidal stabilizer includes an aqueous solution of between 0.1% and 0.4% of polyvinyl alcohol, between 0.6% and 1% of a cationic copolymer of vinylpyrrolidone and of a quaternized vinylimidazol (all percentages being defined by weight relative to the total weight of the colloidal stabilizer). In a particular embodiment, the emulsifier is an anionic or amphiphilic biopolymer, which may be for example chosen from the group consisting of gum Arabic, soy protein, gelatin, sodium caseinate and mixtures thereof.

In a particular embodiment, the shell of the microcapsules is polyurethane-based made from, for example but not limited to polyisocyanate and polyols, polyamide, polyester, etc.

In a particular embodiment, the microcapsules have a polymeric shell resulting from complex coacervation wherein the shell is possibly cross-linked.

In a particular embodiment of the core-shell microcapsules, the core-shell microcapsules comprise an oil-based core comprising a hydrophobic active, preferably at least one compound of formula (I), and a composite shell comprising a first material and a second material, wherein the first material and the second material are different, the first material is a coacervate, the second material is a polymeric material.

In a particular embodiment, the weight ratio between the first material and the second material is comprised between 50:50 and 99.9:0.1.

In a particular embodiment, the coacervate comprises a first polyelectrolyte, preferably selected among proteins (such as gelatin), polypeptides or polysaccharides (such as chitosan), most preferably Gelatin and a second polyelectrolyte, preferably alginate salts, cellulose derivatives guar gum, pectinate salts, carrageenan, polyacrylic and methacrylic acid or xanthan gum, or yet plant gums such as acacia gum (Gum Arabic), most preferably Gum Arabic.

The coacervate first material can be hardened chemically using a suitable cross-linker such as glutaraldehyde, glyoxal, formaldehyde, tannic acid or genipin or can be hardenedenzymatically using an enzyme such as transglutaminase.

The second polymeric material can be selected from the group consisting of polyurea, polyurethane, polyamide, polyester, poly acrylate, polysiloxane, polycarbonate, polysulfonamide, polymers of urea and formaldehyde, melamine and formaldehyde, melamine and urea, or melamine and glyoxal and mixtures thereof, preferably polyurea and/or polyurethane. The second material is preferably present in an amount less than 3 wt. %, preferably less than 1 wt. % based on the total weight of the microcapsule slurry.

The preparation of an aqueous dispersion/slurry of core-shell microcapsules is well known by a skilled person in the art. In a particular embodiment, the microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Missouri U.S.A.), Cytec Industries (West Paterson, New Jersey U.S.A.), Sigma-Aldrich (St. Louis, Missouri U.S.A.).

In a particular embodiment of the core-shell microcapsules, the core-shell microcapsules comprises

- an oil-based core comprising a hydrophobic active, preferably comprising the perfume oil comprising at least one compound of formula (I),
- optionally an inner shell made of a polymerized polyfunctional monomer;
- a biopolymer shell comprising a protein, wherein at least one protein is cross-linked.

According to a particular embodiment, the protein is chosen in the group consisting of milk proteins, caseinate salts such as sodium caseinate or calcium caseinate, casein, whey protein, hydrolyzed proteins, gelatins, gluten, pea protein, soy protein, silk protein and mixtures thereof, preferably sodium caseinate.

According to a particular embodiment, the protein comprises sodium caseinate and a globular protein, preferably chosen in the group consisting of whey protein, beta-lactoglobulin, ovalbumine, bovine serum albumin, vegetable proteins, and mixtures thereof.

The protein is preferably a mixture of sodium caseinate and whey protein.

According to a particular embodiment, the biopolymer shell comprises a crosslinked protein chosen in the group consisting of sodium caseinate and/or whey protein.

According to a particular embodiment, the microcapsules slurry comprises at least one microcapsule made of:

- an oil-based core comprising the hydrophobic active, preferably comprising the perfume oil comprising at least one compound of formula (I);
- an inner shell made of a polymerized polyfunctional monomer; preferably a polyisocyanate having at least two isocyanate functional groups
- a biopolymer shell comprising a protein, wherein at least one protein is cross-linked;
- wherein the protein contains preferably a mixture comprising sodium caseinate and a globular protein, preferably whey protein.
- optionally at least an outer mineral layer.

According to an embodiment, sodium caseinate and/or whey protein is (are) cross-linked protein(s).

The weight ratio between sodium caseinate and whey protein is preferably comprised between 0.01 and 100, preferably between 0.1 and 10, more preferably between 0.2 and 5.

In a particular embodiment, the microcapsules is a one-shell aminoplast core-shell microcapsule obtainable by a process comprising the steps of:

1) admixing a perfume oil with at least a polyisocyanate having at least two isocyanate functional groups to form an oil phase;
2) dispersing or dissolving into water an aminoplast resin and optionally a stabilizer to form a water phase;
3) preparing an oil-in-water dispersion, wherein the mean droplet size is comprised between 1 and 100 microns, by admixing the oil phase and the water phase;

4) performing a curing step to form the wall of said microcapsule; and optionally drying the final dispersion to obtain the dried core-shell microcapsule.

In a particular embodiment, the core-shell microcapsule is a formaldehyde-free capsule. A typical process for the preparation of aminoplast formaldehyde-free microcapsules slurry comprises the steps of 1) preparing an oligomeric composition comprising the reaction product of, or obtainable by reacting together:
   a. a polyamine component in the form of melamine or of a mixture of melamine and at least one $C_1$-$C_4$ compound comprising two $NH_2$ functional groups;
   b. an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
   c. a protic acid catalyst;
2) preparing an oil-in-water dispersion, wherein the droplet size is comprised between 1 and 600 microns, and comprising:
   a. an oil;
   b. a water medium:
   c. at least an oligomeric composition as obtained in step 1;
   d. at least a cross-linker selected amongst:
      i. $C_4$-$C_{12}$ aromatic or aliphatic di- or tri-isocyanates and their biurets, triurets, trimmers, trimethylol propane-adduct and mixtures thereof; and/or
      ii. a di- or tri-oxiran compounds of formula:

Q-(oxiran-2-ylmethyl)$_n$ wherein n stands for 2 or 3 and Q represents a $C_2$-$C_6$ group optionally comprising from 2 to 6 nitrogen and/or oxygen atoms;
   e. optionally a $C_1$-$C_4$ compounds comprising two $NH_2$ functional groups;
3) Heating the dispersion; and
4) Cooling the dispersion.

The above process is described in more details in WO 2013/068255.

In a particular embodiment of the core-shell microcapsules, the core-shell microcapsule is a polyamide core-shell polyamide microcapsule comprising:

an oil based core comprising an hydrophobic active, preferably comprising at least one compound of formula (I), and
a polyamide shell comprising or being obtainable from:
   an acyl chloride,
   a first amino compound, and
   a second amino compound.

According to a particular embodiment, the polyamide core-shell microcapsule comprises:

an oil based core comprising an hydrophobic active, preferably comprising at least one compound of formula (I), and
a polyamide shell comprising or being obtainable from:
   an acyl chloride, preferably in an amount comprised between 5 and 98%, preferably between 20 and 98%, more preferably between 30 and 85% w/w
   a first amino compound, preferably in an amount comprised between 1% and 50% w/w, preferably between 7 and 40% w/w;
   a second amino compound, preferably in an amount comprised between 1% and 50% w/w, preferably between 2 and 25% w/w
   a stabilizer, preferably a biopolymer, preferably in an amount comprised between 0 and 90%, preferably between 0.1 and 75%, more preferably between 1 and 70%.

According to a particular embodiment, the polyamide core-shell microcapsule comprises:

an oil based core comprising a hydrophobic active, preferably comprising the perfume oil comprising at least one compound of formula (I), and
a polyamide shell comprising or being obtainable from:
   an acyl chloride,
   a first amino-compound being an amino-acid, preferably chosen in the group consisting of L-Lysine, L-Arginine, L-Histidine, L-Tryptophane and/or mixture thereof
   a second amino compound chosen in the group consisting of ethylene diamine, diethylene triamine, cystamine and/or mixture thereof, and
   a biopolymer chosen in the group consisting of casein, sodium caseinate, bovin serum albumin, whey protein, and/or mixture thereof.

The first amino-compound can be different from the second amino-compound.

Typically, a process for preparing a polyamide-based micrcoapsule includes the following steps:

a) Dissolving at least one acyl chloride in a hydrophobic material, preferably a perfume to form an oil phase;
b) Dispersing the oil phase obtained in step a) into a water phase comprising a first amino compound to form an oil-in water emulsion;
c) Performing a curing step to form polyamide microcapsules in the form of a slurry;

wherein a stabilizer is added in the oil phase and/or in the water phase, and
wherein at least a second amino-compound is added in the water phase before the formation of the oil-in-water emulsion and/or in the oil-in water emulsion obtained after step b).

In a particular embodiment, the shell of the microcapsule is polyurea- or polyurethane-based. Examples of processes for the preparation of polyurea and polyureathane-based microcapsule slurry are for instance described in WO 2007/004166, EP 2300146, and EP 2579976. Typically a process for the preparation of polyurea or polyurethane-based microcapsule slurry include the following steps:

a) Dissolving at least one polyisocyanate having at least two isocyanate groups in an oil to form an oil phase;
b) Preparing an aqueous solution of an emulsifier or colloidal stabilizer to form a water phase;
c) Adding the oil phase to the water phase to form an oil-in-water dispersion, wherein the mean droplet size is comprised between 1 and 500 μm, preferably between 5 and μm; and
d) Applying conditions sufficient to induce interfacial polymerisation and form microcapsules in form of a slurry.

In a particular embodiment, the microcapsule can be in form of a powder, which in particular may be obtained by submitting the microcapsule slurry to a drying, like spray-drying, to provide the microcapsules as such, i.e. in a powdery form. It is understood that any standard method known by a person skilled in the art to perform such drying is also applicable. In particular the slurry may be spray-dried preferably in the presence of a polymeric carrier material such as polyvinyl acetate, polyvinyl alcohol, dextrins, natural or modified starch, gum Arabic, vegetable gums, pectins, xanthans, alginates, carrageenans or cellulose derivatives to provide microcapsules in a powder form.

However, one may cite also other drying method such as the extrusion, plating, spray granulation, the fluidized bed, or even a drying at room temperature using materials (carrier, desiccant) that meet specific criteria as disclosed in WO 2017/134179.

The proportions in which the compounds of formula (I) can be incorporated into perfumed consumer product vary within a wide range of values. These values are dependent on the nature of the article to be perfumed and on the desired organoleptic effect as well as on the nature of the co-ingredients when the compounds according to the invention are mixed with perfuming co-ingredient(s), perfumery carrier(s) or perfumery adjuvant (s) commonly used in the art.

Typical concentrations of compound of formula (I) are in the order of 0.0001% to 5% by weight, or even more, of the compounds of the invention based on the weight of the consumer product into which they are incorporated. Particularly, the compound of formula (I) may be incorporated in the perfumed consumer product at a concentration comprised between 0.0050% and 1% based on the weight of the consumer product.

A last object of the present invention is method of imparting a long-lasting or substantive green odor to surfaces, such as skin or hair, by adding at least one compound of formula (I) as defined in claim 1 to perfuming compositions or perfumed consumer products and applying them to the corresponding targeted surface.

The compounds of formula (I) can be prepared according to a method reported in the literature or standard methods known in the art as described herein-below. The invention's perfumed consumer product can be prepared according to a method reported in the literature or standard methods known in the art as described herein-below.

EXAMPLES

The invention will now be described in further detail by way of the following examples, wherein the abbreviations have the usual meaning in the art, the temperatures are indicated in degrees centigrade (° C.). NMR spectra were acquired using either a Bruker Avance II Ultrashield 400 plus operating at 400 MHz, ($^1$H) and 100 MHz ($^{13}$C) or a Bruker Avance III 500 operating at 500 MHz ($^1$H) and 125 MHz ($^{13}$C) or a Bruker Avance III 600 cryoprobe operating at 600 MHz ($^1$H) and 150 MHz ($^{13}$C). Spectra were internally referenced relative to tetramethyl silane 0.0 ppm. $^1$H NMR signal shifts are expressed in δ ppm, coupling constants (J) are expressed in Hz with the following multiplicities: s, singlet; d, doublet; t, triplet; q, quartet; m, multiplet; b, broad (indicating unresolved couplings) and were interpreted using Bruker Topspin software. 13C NMR data are expressed in chemical shift δ ppm and hybridization from DEPT 90 and DEPT 135 experiments, C, quaternary; CH, methine; $CH_2$, methylene; $CH_3$, methyl.

All experimental evaporations were carried out on a precision hotplate Prezitherm PZ72 by Harry Gestigkeit GmbH or equivalent using lightweight aluminum crucibles (TA instruments Tzero hermetic lid or equivalent [Part no. 901671.901]). The GC/MS analytical analyses were carried out on Agilent Gas Chromatograph 7890B coupled to an Agilent MS detector 5977B. The direct injections were done using the standard Agilent inlet with Agilent liner 5190-2293. The dynamic headspace evaluations were done using Gerstel Cooled Injection System inlet cryo-cooled with CCD2. This inlet is mounted with Thermal Desorption Unit 2 allowing heated desorption of sample while cryofocusing on the CIS before separation in the column. This setup requires use of sample traps Tenax TA (Gerstel 020810-005-00 or Supelco 6484U). The column used for separation was Agilent J&W DB-1 ms Ultra Inert GC Column with dimensions: 20 m length, 0.18 mm id, 0.18 μm film thickness, 7 inch cage [Part no. 121-0122U1].

Example 1

Preparation of Compounds of Formula (I)

Synthesis of (2E,6Z)-nona-2,6-dien-1-yl hexadecanoate

The title compound was prepared by two procedures described below.

Palmitoyl chloride (20 g, 72.7 mmol), dissolved in 50 ml of $CH_2Cl_2$, was added dropwise over 1 h to a cold (ice bath) $CH_2Cl_2$ (150 ml) solution of triethyl amine (8.1 g, 80 mmol), 4-dimethylaminopyridine (1.8 g, 14.7 mmol) and (2E,6Z)-nona-2,6-dien-1-ol (12.3 g, 87.4 mmol). The reaction mixture was removed from the cold bath and stirred at rt for 20 h. The mixture was carefully poured into 1M HCl (300 ml) and then extracted with diethyl ether (2×300 ml). The combined organic phases were washed with water, sat. $Na_2CO_3$ and water. The organic phases were combined, dried over $Na_2SO_4$, filtered and concentrated. The resulting material was subjected to flash chromatography (silica gel, hexane/EtOAc, 100:0 to 98:2) affording 20.2 g (53.3 mmol, 73% yield) of (2E,6Z)-nona-2,6-dien-1-yl hexadecanoate as a pale-yellow oil.

$^1$H NMR ($CDCl_3$, 500 MHz): δ 0.88 (t, J=7.0 Hz, 3H), 0.95 (t, J=7.5 Hz, 3H), 1.21-1.34 (m, 24H), 1.59-1.65 (m, 2H), 2.03 (quint, J=7.5 Hz, 2H), 2.07-2.16 (m, 4H), 2.30 (t, J=7.6 Hz, 2H), 4.51 (d, J=6.4 Hz, 2H), 5.26-5.35 (m, 1H), 5.36-5.43 (m, 1H), 5.58 (dt, J=15.4, 6.4 Hz, 1H), 5.77 (dt, J=15.4, 6.3 Hz, 1H).

$^{13}$C NMR ($CDCl_3$, 125.8 MHz): δ 14.12 ($CH_3$), 14.29 ($CH_3$), 20.56 ($CH_2$), 22.70 ($CH_2$), 24.99 ($CH_2$), 26.53 ($CH_2$), 29.17 ($CH_2$), 29.28 ($CH_2$), 29.37 ($CH_2$), 29.48 ($CH_2$), 29.61 ($CH_2$), 29.67 ($CH_2$), 29.69 ($CH_2$), 29.70 ($CH_2$), 31.94 ($CH_2$), 32.34 ($CH_2$), 34.38 ($CH_2$), 64.97 ($CH_2$), 124.29 (CH), 127.93 (CH), 132.32 (CH), 135.67 (CH), 173.68 (C).

Methyl palmitate, (2E,6Z)-nona-2,6-dien-1-ol and 1,8-diazabicyclo [5.4.0]undec-7-ene (DBU) were added to a 100-ml flask equipped with a distillation head. The mixture was heated in a 150° C. oil bath for 4 h while allowing MeOH to distill from the flask. The excess pelargodienol was removed by vacuum distillation from the reaction mixture (vapor temp. 20 mTorr). The remaining residue was diluted in ethyl acetate and washed with water (3×). The organic phase was dried over $Na_2SO_4$, filtered and concentrated. The residue was further concentrated by heating under vacuum (200° C., 20 mTorr) to remove residual methyl palmitate. The material then was dissolved in diethyl ether and filtered through a bed of silica gel. Concentrating under vacuum afforded 9.51 g (52% yield) of (2E,6Z)-nona-2,6-dien-1-yl hexadecanoate as a pale-amber oil.

Synthesis of (2E,6Z)-nona-2,6-dien-1-yl tetradecanoate

Following the procedure described for (2E,6Z)-nona-2,6-dien-1-yl hexadecanoate, the title compound was prepared from tetradecanoyl chloride (5.0 g, 20.3 mmol) and (2E, 6Z)-nona-2,6-dien-1-ol (3.41 g, 24.3 mmol) and isolated by silica gel flash chromatography as a colorless oil (6.2 g, 87% yield).

$^1$H NMR (CDCl$_3$, 500 MHz): δ 0.88 (t, J=6.8 Hz, 3H), 0.95 (t, J=7.6 Hz, 3H), 1.21-1.35 (m, 1.57-1.67 (m, 2H), 2.03 (quint, J=7.5 Hz, 2H), 2.07-2.16 (m, 4H), 2.30 (t, J=7.5 Hz, 2H), 4.51 (d, J=6.5 Hz, 2H), 5.27-5.34 (m, 1H), 5.36-5.42 (m, 1H), 5.58 (dt, J=15.4, 6.4 Hz, 1H), 5.77 (dt, J=15.4, 6.4 Hz, 1H).

$^{13}$C NMR (CDCl$_3$, 125.8 MHz): δ 14.1 (CH$_3$), 14.3 (CH$_3$), 20.6 (CH$_2$), 22.7 (CH$_2$), 25.0 (CH$_2$), 26.5 (CH$_2$), 29.2 (CH$_2$), 29.3 (CH$_2$), 29.4 (CH$_2$), 29.5 (CH$_2$), 29.6 (CH$_2$), 29.67 (CH$_2$), 29.7 (CH$_2$), 31.9 (CH$_2$), 32.4 (CH$_2$), 34.4 (CH$_2$), 65.0 (CH$_2$), 124.3 (CH), 127.9 (CH), 132.3 (CH), 135.7 (CH), 173.7 (C).

Synthesis of (2E,6Z)-nona-2,6-dien-1-yl dodecanoate

Following the procedure described for (2E,6Z)-nona-2,6-dien-1-yl hexadecanoate, the title compound was prepared from dodecanoyl chloride (5 g, 22.4 mmol) and (2E,6Z)-nona-2,6-dien-1-ol (3.77 g, 26.9 mmol) and isolated by silica gel flash chromatography as a colorless oil (5.85 g, 81% yield).

$^1$H NMR (CDCl$_3$, 500 MHz): δ 0.88 (t, J=6.9 Hz, 3H), 0.95 (t, J=7.6 Hz, 3H), 1.20-1.35 (m, 16H), 1.58-1.66 (m, 2H), 2.03 (quint, J=7.5 Hz, 2H), 2.07-2.16 (m, 4H), 2.30 (t, J=7.5 Hz, 2H), 4.51 (d, J=6.5 Hz, 2H), 5.27-5.35 (m, 1H), 5.35-5.43 (m, 1H), 5.58 (dt, J=15.4, 6.4 Hz, 1H), 5.77 (dt, J=15.4, 6.4 Hz, 1H).

$^{13}$C NMR (CDCl$_3$, 125.8 MHz): δ 14.1 (CH$_3$), 14.3 (CH$_3$), 20.6 (CH$_2$), 22.7 (CH$_2$), 25.0 (CH$_2$), 26.5 (CH$_2$), 29.2 (CH$_2$), 29.3 (CH$_2$), 29.4 (CH$_2$), 29.5 (CH$_2$), 29.6 (CH$_2$), 31.9 (CH$_2$), 32.4 (CH$_2$), 34.4 (CH$_2$), 65.0 (CH$_2$), 124.3 (CH), 127.9 (CH), 132.3 (CH), 135.7 (CH), 173.7 (C).

Synthesis of (2E,6Z)-nona-2,6-dien-1-yl benzoate—Comparative compound

Following the procedure described for (2E,6Z)-nona-2,6-dien-1-yl hexadecanoate, the title compound was prepared from benzoyl chloride (10 g, 71.1 mmol) and (2E,6Z)-nona-2,6-dien-1-ol (12.0 g, 85.4 mmol) and isolated by silica gel flash chromatography as a colorless oil (16.3 g, 94% yield).

$^1$H NMR (CDCl$_3$, 500 MHz): δ 0.95 (t, J=7.5 Hz, 3H), 2.04 (quint, J=7.5 Hz, 2H), 2.11-2.18 (m, 4H), 4.77 (d, J=6.4 Hz, 2H), 5.26-5.36 (m, 1H), 5.37-5.43 (m, 1H), 5.70 (dt, J=15.3, 6.4 Hz, 1H), 5.87 (dt, J=15.3, 6.4 Hz, 1H), 7.43 (t, J=7.8 Hz, 2H), 7.52-7.57 (m, 1H), 8.04-8.07 (m, 2H).

$^{13}$C NMR (CDCl$_3$, 125.8 MHz): δ 14.3 (CH$_3$), 20.6 (CH$_2$), 26.5 (CH$_2$), 32.4 (CH$_2$), 65.6 (CH$_2$), 124.2 (CH), 127.9 (CH), 128.3 (CH), 129.6 (CH), 130.4 (C), 132.4 (CH), 132.9 (CH), 135.8 (CH), 166.4 (C).

Example 2

Reaction Rate Measurement (in Solution) of the Invention's Compound and Comparative Compound The release kinetics of 3,7-dimethyl-2,6-octadien-1-yl hexadecanoate (comparative compound) and (2E,6Z)-nona-2,6-dien-1-yl hexadecanoate (invention's compound) in the presence of a hydrolase were compared.

In order to compare the reaction rate of the esters, the amount of 3,7-dimethyl-2,6-octadien-1-yl hexadecanoate and (2E,6Z)-nona-2,6-dien-1-yl hexadecanoate and the amount of ethyl hexadecanoate over time were measured by GC/MS. The ethyl hexadecanoate was formed by the reaction between the hexadecanoic acid released and the ethanol.

Enzyme Solution Preparation: The lipase enzyme source used was Enzyme Innovation Addclean LP L at an activity of 20000 Lipase Units/g. A stock solution of 100 LU/ml was prepared and diluted in serial dilution to working concentrations as follows:

| Solution | Condition | Lipase (g) | In H2O (ml) | LU/ml |
|---|---|---|---|---|
| A | 0.5% Lipase | 0.05 | 10 | 100.00 |
| B | Then 1 ml of A to 10 ml | 1 | 9 | 10 |
| C | Then 1 ml of B to 10 ml | 1 | 9 | 1 |
| D | Then 1 ml of C to 10 ml | 1 | 9 | 0.1 |
| E | Then 1 ml of D to 10 ml | 1 | 9 | 0.01 |

The solutions comprising 3,7-dimethyl-2,6-octadien-1-yl hexadecanoate or (2E,6Z)-nona-2,6-dien-1-yl hexadecanoate (also called palmitate ester solutions) were prepared by dissolving in ethanol to 5% by weight. These were subsequently diluted to working conditions of the experiment.

In a 2 ml Agilent GC vial (Agilent 5183-2068), 50 ul of 100 LU/ml solution was added with a micropipette. 100 ul deionized water was added to ensure continued hydrolysis. Samples to were prepared for each time condition, replicate, and palmitate ester solutions of interest because the reaction will be stopped and only measured once at 0 hours, 0.5 hours and 1 hour. An additional two samples were prepared with only 150 ul deionized water as a negative control.

The palmitate esters were prepared by dissolving in ethanol to 5% by weight (stock). Palmitate ester solution was further diluted to 0.2% and 50 ul added to all sample vials above and recorded as time zero. The sample vials remained open to the air on the precision hotplate preheated to 32C. At 0 hours, 0.5 hours, and 1 hour 800 ul of Ethanol was added to their respective vials to stop the reaction. Vials were closed and mixed by shaking. Samples were analyzed by GC/MS direct injection methodology as follows.

GC-MS analyses were performed on an Agilent Gas Chromatograph system 7890B coupled to an Agilent Mass Selective Detector 5977B and equipped with a Gerstel MPS autosampler or equivalent. Chromatographic separation was achieved using an Agilent J&W DB-1 ms Ultra Inert Capillary GC Column with a length of 20 m, an inner diameter of 0.18 mm, a film thickness of 0.18 μm [Part no. 121-0122U1]. Helium was used to elute the volatiles at a constant flow of 1.2 mL/min using a temperature gradient increasing from 50° C. (hold for 2 min) to 300° C. at a rate of 15° C./min with a final hold time of 2 min (yielding a total runtime of 20.667 min). Solution preparations were injected with an injection of 1 μL (using a 10-μL syringe) into an Agilent inlet (Inlet 1). An Agilent 5190-2293 inlet liner was inserted into Inlet 1, and splitless mode was used with the injector set at 250° C. Mass Spectrometer was operated in scan mode of mass 48 to 350. External calibration curves of (2E,6Z)-nona-2,6-dien-1-yl hexadecanoate and 3,7-dimethyl-2,6-octadien-1-yl hexadecanoate were prepared at 10-500 ppm was prepared and sample signal quantified in ppm. Analysis produced the results as showed in FIGS. 1 and 2.

Figure 2:
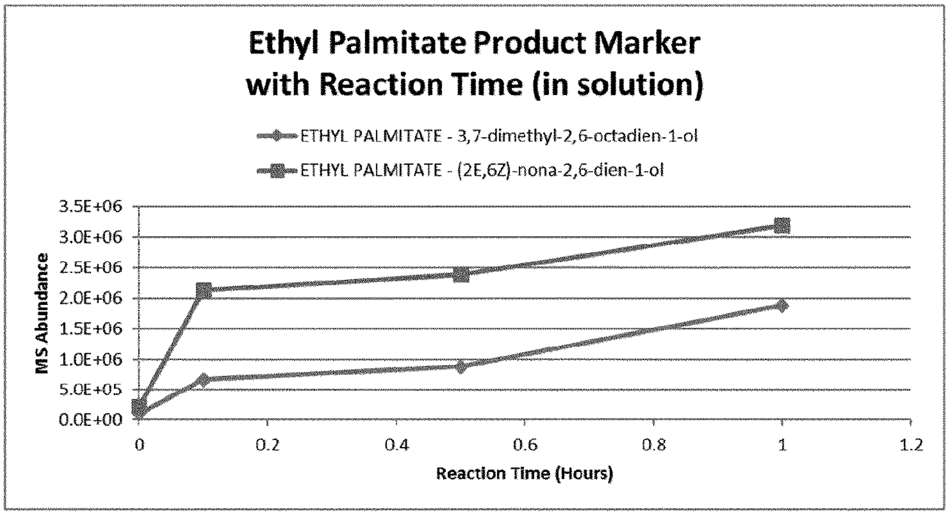
FIG. 2: Analysis of the concentration of ethyl hexadecanoate released from 3,7-dimethyl-2,6-octadien-1-yl hexadecanoate and (2E,6Z)-nona-2,6-dien-1-yl hexadecanoate in solution in function of time.

As shown in FIG. 1, the concentration in solution of (2E,6Z)-nona-2,6-dien-1-yl hexadecanoate decreased more rapid than the concentration of 3,7-dimethyl-2,6-octadien-1-yl hexadecanoate. As the released hexadecanoic acid reacted with ethanol present in solution, the increase of ethyl hexadecanoate, as shown in FIG. 2, confirmed the faster release of (2E,6Z)-nona-2,6-dien-1-ol compared to 3,7-dimethyl-2,6-octadien-1-ol. The combination of more rapid loss of reactant and more rapid buildup of ethyl hexandecanoate shows a higher total rate of lipase-catalyzed reaction for the (2E,6Z)-nona-2,6-dien-1-ylhexadecanoate than 3,7-dimethyl-2,6-octadien-1-ylhexadecanoate.

Example 3

Fragrance Evolution on Tzero Lids (Dynamic Headspace) of the Invention's Compound and Comparative Compounds To further investigate the release kinetics of palmitate esters in the presence of hydrolases, an in-vitro assay measuring the functional perfume ingredient in the gaseous phase was devised.

Three palmitate esters releasing respectively (2E,6Z)-nona-2,6-dien-1-ol (corresponding to invention's compound) and 3,7-dimethyl-2,6-octadien-1-ol (corresponding to comparative compound) were tested in the presence of physiologically relevant concentration of Hydrolase (0.1 LU/ml) as follows. 2.5 ul Lipase solution (0.100 LU/ml) was added to Tzero Lids TA [Part no. 901671.901] crucibles. 2.5 ul of 0%, 0.5%, 0.1%, 0.5% and 1% solution in ethanol of palmitate esters were added to the same crucibles and placed on preheated precision hotplate to 32C. Additional aliquots of 2.5 ul water were added to the crucibles at 1 h and 4 h to simulate humidity on skin and facilitate hydrolysis. The crucibles were transferred to 20 ml headspace vials after X hours at 32C.

Analysis performed by Dynamic Headspace using Tenax TA trap outlined as follows. GC-MS-DHS analyses were performed on an Agilent Gas Chromatograph system 7890B coupled to an Agilent Mass Selective Detector 5977B and equipped with a Gerstel MPS autosampler. Additionally equipment of automated Gerstel Dynamic Headspace System, ATEX air sampling tube gripper for 20 mL headspace vials with a metal screw cap (preassembled with 1.3 mm PTFE septa) and Gerstel CIS 4C cryostatic cooling device CCD2 (Inlet 2) mounted with Gerstel TDU2 thermal desorption unit. Purge and Trap Dynamic Headspace technique was used for performing GC headspace analysis with a purge volume of 20 mL at a rate of 100 mL $min^{-1}$ at 32° C. and a trap volume of 30 mL at a rate of 5 mL $min^{-1}$ at 32° C. TDU desorption mode was set to splitless for desorbing TDU tube Tenax TA Gerstel 020810-005-00 or Supelco 6484U air sampling trap in TDU2 using a temperature gradient increasing from 25° C. (hold for 0.3 min) to 270° C. at a rate of 240° C. $min^{-1}$ with a final hold time of 5 min. A CIS 4C Gerstel Tenax TA 013247-005-00 or Supelco 6823-U liner was used with temperature gradient increasing from −10° C. (hold for 0.5 min) to 300° C. at a rate of 12° C. min with a final hold time of 10 min. Solvent vent mode was used with a purge flow of at 50 mL $min^{-1}$ at 7 min and a vent flow of 50 mL $min^{-1}$ until 0 min. Chromatographic separation was achieved using an Agilent J&W DB-1 ms Ultra Inert Capillary GC Column with a length of 20 m, an inner diameter of 0.18 mm, a film thickness of 0.18 μm [Part no. 121-0122U1]. Helium was used to elute the volatiles at a constant flow of 1.2 mL/min using an oven temperature program as follows: 50° C. (hold for 2 min) increased to 300° C. at a rate of 10° C. $min^{-1}$ with a final hold time of 3 min. Mass Spectrometer was operated in scan mode of mass 48 to 350.

Control is the weight equivalent of (2E,6Z)-nona-2,6-dien-1-ol (corresponding to the released compound from the invention's compound) and 3,7-dimethyl-2,6-octadien-1-ol (corresponding to the release compound from the comparative compound) Standard curves are prepared by diluting and spiking controls on blank Tenax traps.

Figure 3:
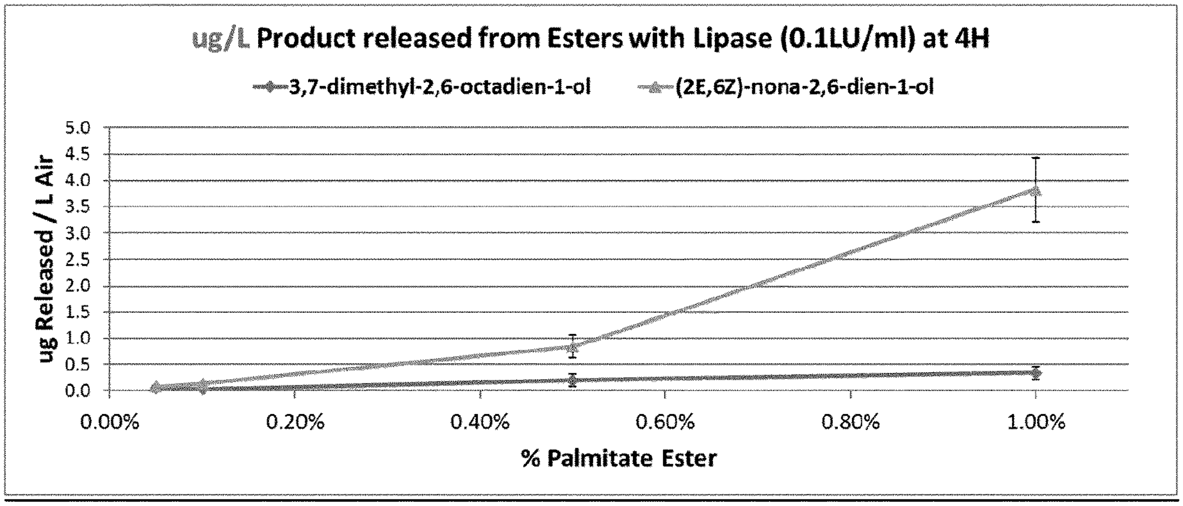
FIG. 3: Analysis of the concentration of 3,7-dimethyl-2,6-octadien-1-ol and (2E,6Z)-nona-2,6-dien-1-ol in sample headspace after 4 hours on a surface as a function of respective ester concentration 3,7-dimethyl-2,6-octadien-1-yl hexadecanoate and (2E,6Z)-nona-2,6-dien-1-yl hexadecanoate.

The results of the released alcohols in headspace at 4 hours are shown in FIG. 3.

It was observed that (2E,6Z)-nona-2,6-dien-1-yl hexadecanoate releases it fragrance materials at higher rate than 3,7-dimethyl-2,6-octadien-1-yl hexadecanoate.

Example 4

Fragrance Evolution on Tzero Lids (Dynamic Headspace) of the Invention's Compound and Comparative Compounds To further investigate the impact of the "R" group on the release kinetics the ester in the presence of hydrolases, an in-vitro assay measuring the functional perfume ingredient in the gaseous phase was devised.

Four esters releasing (2E,6Z)-nona-2,6-dien-1-ol (corresponding to invention's compound) were tested. (2E,6Z)-nona-2,6-dien-1-yl hexadecanoate, (2E,6Z)-nona-2,6-dien-1-yl tetradecanoate, (2E,6Z)-nona-2,6-dien-1-yl dodecanoate and (2E,6Z)-nona-2,6-dien-1-yl benzoate (comparative compound). Testing was done in the presence of physiologically relevant concentration of Hydrolase (0.1 LU/ml) as follows. 2.5 ul Lipase solution (0.100 LU/ml) was added to Tzero Lids TA [Part no. 901671.901] crucibles. 2.5 ul of 1% solution in ethanol of palmitate esters were added to the same crucibles and placed on preheated precision hotplate to 32C. Additional aliquots of 2.5 ul water were added to the crucibles at 1 h and 4 h to simulate humidity on skin and facilitate hydrolysis. The crucibles were transferred to 20 ml headspace vials after 4 hours at 32C.

Analysis performed by Dynamic Headspace using Tenax TA trap outlined as follows. GC-MS-DHS analyses were performed on an Agilent Gas Chromatograph system 7890B coupled to an Agilent Mass Selective Detector 5977B and equipped with a Gerstel MPS autosampler. Additionally equipment of automated Gerstel Dynamic Headspace System, ATEX air sampling tube gripper for 20 mL headspace vials with a metal screw cap (preassembled with 1.3 mm PTFE septa) and Gerstel CIS 4C cryostatic cooling device CCD2 (Inlet 2) mounted with Gerstel TDU2 thermal desorption unit. Purge and Trap Dynamic Headspace technique was used for performing GC headspace analysis with a purge volume of 20 mL at a rate of 100 mL $min^{-1}$ at 32° C. and a trap volume of 30 mL at a rate of mL $min^{-1}$ at 32° C. TDU desorption mode was set to splitless for desorbing TDU tube Tenax TA Gerstel 020810-005-00 or Supelco 6484U air sampling trap in TDU2 using a temperature gradient increasing from 25° C. (hold for 0.3 min) to 270° C. at a rate of 240° C. min with a final hold time of 5 min. A CIS 4C Gerstel Tenax TA 013247-005-00 or Supelco 6823-U liner was used with temperature gradient increasing from −10° C. (hold for 0.5 min) to 300° C. at a rate of 12° C. $min^{-1}$ with a final hold time of 10 min. Solvent vent mode was used with a purge flow of at 50 mL $min^{-1}$ at 7 min and a vent flow of 50 mL $min^{-1}$ until 0 min. Chromatographic separation was achieved using an Agilent J&W DB-1 ms Ultra Inert Capillary GC Column with a length of 20 m, an inner diameter of 0.18 mm, a film thickness of 0.18 μm [Part no. 121-0122U1]. Helium was used to elute the volatiles at a constant flow of 1.2 mL/min using an oven temperature program as follows: 50° C. (hold for 2 min) increased to 300° C. at a rate of 10° C. $min^{-1}$ with a final hold time of 3 min. Mass Spectrometer was operated in scan mode of mass 48 to 350.

Control is the weight equivalent of (2E,6Z)-nona-2,6-dien-1-ol (corresponding to the released compound from the invention's compound). Standard curves are prepared by diluting and spiking controls on blank Tenax traps.

Figure 4:
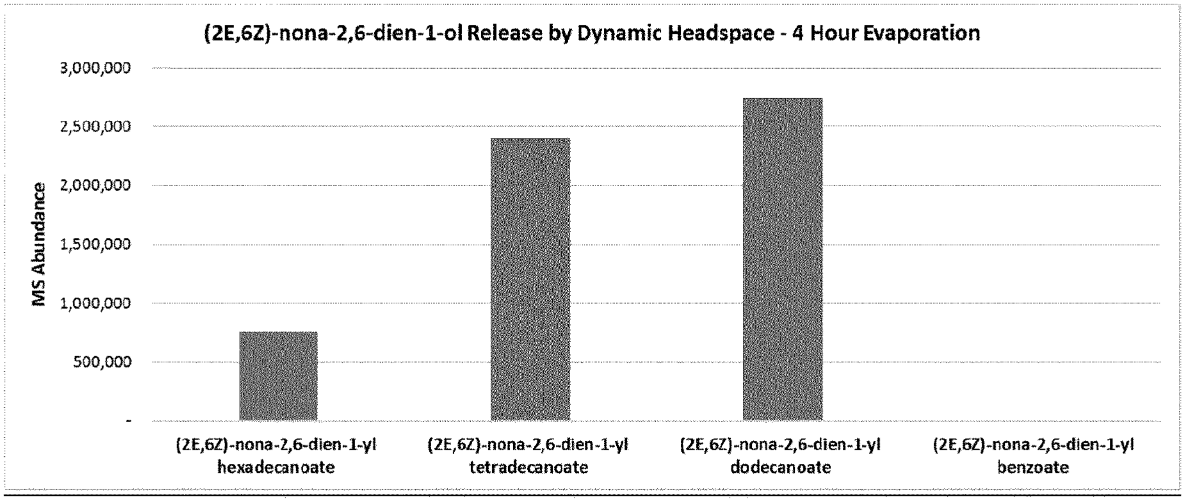
FIG. 4: Analysis of the abundance of (2E,6Z)-nona-2,6-dien-1-ol in headspace after 4 hours evaporation on a surface as a function of ester structures (2E,6Z)-nona-2,6-dien-1-yl hexadecanoate, (2E,6Z)-nona-2,6-dien-1-yl tetradecanoate, (2E,6Z)-nona-2,6-dien-1-yl dodecanoate and (2E,6Z)-nona-2,6-dien-1-yl benzoate.

The results of the released (2E,6Z)-nona-2,6-dien-1-ol from (2E,6Z)-nona-2,6-dien-1-yl hexadecanoate, (2E,6Z)-nona-2,6-dien-1-yl tetradecanoate, (2E,6Z)-nona-2,6-dien-1-yl dodecanoate and (2E,6Z)-nona-2,6-dien-1-yl benzoate in headspace at 4 hours are shown in FIG. 4.

It was observed that compounds having a R group being a $C_{11}$ linear alkyl chain, a $C_{13}$ linear alkyl chain or a C15 linear alkyl chain, release (2E,6Z)-nona-2,6-dien-1-ol while the compound having a R group being benzoate does not.

Example 5

Fragrance Evolution on Tzero Lids (Dynamic Headspace) of the Invention's Compound in a Personal Care Base To confirm fragrance release in presence of personal care base, personal care base was formulated with invention's compound and analyzed by an in-vitro assay measuring the functional perfume ingredient in the gaseous phase.

TABLE 1

Composition of a typical day cream base O/W emulsion.

| Phase | Ingredients | Amount [wt %] |
|---|---|---|
| A | Steareth-2 (and) PEG-8 Distearate[1] | 5.0 |
| | Cetyl alcohol | 0.5 |
| | Ceteth-20 (and) glyceryl stearate (and) PEG-6 stearate (and) Steareth-20 [2] | 4.0 |
| | Squalan [3] | 1.0 |
| | Paraffin oil [4] | 2.0 |
| | Petrolatum [5] | 5.5 |
| B | Deionized water | 75.2 |
| | Propylene glycol | 5.0 |
| C | Phenoxyethanol (and) Piroctone olamine [6] | 0.6 |
| D | Sodium carbomer [7] | 0.2 |
| E | Compound of formula (I) | 1 |

(1) Arlacel ® 985; origin: Croda
(2) Tefose ® 2561; origin: Gattefossé
(3) Biolip P 90; origin: Gattefossé
(4) Mineral oil 30-40 CPS
(5) Petroleum jelly
(6) Nipaguard ® PO 5; origin: Clariant
(7) PNC 400

Testing was done in the presence of physiologically relevant concentration of Hydrolase (0.1 LU/ml) as follows. 2.5 ul Lipase solution (0.100 LU/ml) was added to Tzero Lids TA [Part no. 901671.901] crucibles. 2.5 ul of personal care base with (2E,6Z)-nona-2,6-dien-1-yl hexadecanoate was added to the same crucibles and placed on preheated precision hotplate to 32C. Additional aliquots of 2.5 ul water were added to the crucibles at 1 h and 4 h to simulate humidity on skin and facilitate hydrolysis. The crucibles were transferred to 20 ml headspace vials after 4 hours at 32C.

Analysis performed by Dynamic Headspace using Tenax TA trap outlined as follows. GC-MS-DHS analyses were performed on an Agilent Gas Chromatograph system 7890B coupled to an Agilent Mass Selective Detector 5977B and equipped with a Gerstel MPS autosampler. Additionally equipment of automated Gerstel Dynamic Headspace System, ATEX air sampling tube gripper for 20 mL headspace vials with a metal screw cap (preassembled with 1.3 mm PTFE septa) and Gerstel CIS 4C cryostatic cooling device CCD2 (Inlet 2) mounted with Gerstel TDU2 thermal desorption unit. Purge and Trap Dynamic Headspace technique was used for performing GC headspace analysis with a purge volume of 20 mL at a rate of 100 mL $min^{-1}$ at 32° C. and a trap volume of 30 mL at a rate of mL $min^{-1}$ 1 at 32° C. TDU desorption mode was set to splitless for desorbing TDU tube Tenax TA Gerstel 020810-005-00 or Supelco 6484U air sampling trap in TDU2 using a temperature gradient increasing from 25° C. (hold for 0.3 min) to 270° C. at a rate of 240° C. $min^{-1}$ with a final hold time of 5 min. A CIS 4C Gerstel Tenax TA 013247-005-00 or Supelco 6823-U liner was used with temperature gradient increasing from −10° C. (hold for 0.5 min) to 300° C. at a rate of 12° C. $min^{-1}$ with a final hold time of 10 min. Solvent vent mode was used with a purge flow of at 50 mL $min^{-1}$ at 7 min and a vent flow of 50 mL $min^{-1}$ until 0 min. Chromatographic separation was achieved using an Agilent J&W DB-1 ms Ultra Inert Capillary GC Column with a length of 20 m, an inner diameter of 0.18 mm, a film thickness of 0.18 μm [Part no. 121-0122UI]. Helium was used to elute the volatiles at a constant flow of 1.2 mL/min using an oven temperature program as follows: 50° C. (hold for 2 min) increased to 300° C. at a rate of 10° C. $min^{-1}$ with a final hold time of 3 min. Mass Spectrometer was operated in scan mode of mass 48 to 350.

Control is the weight equivalent of (2E,6Z)-nona-2,6-dien-1-ol (corresponding to the released compound from the invention's compound). Standard curves are prepared by diluting and spiking controls on blank Tenax traps.

Figure 5:
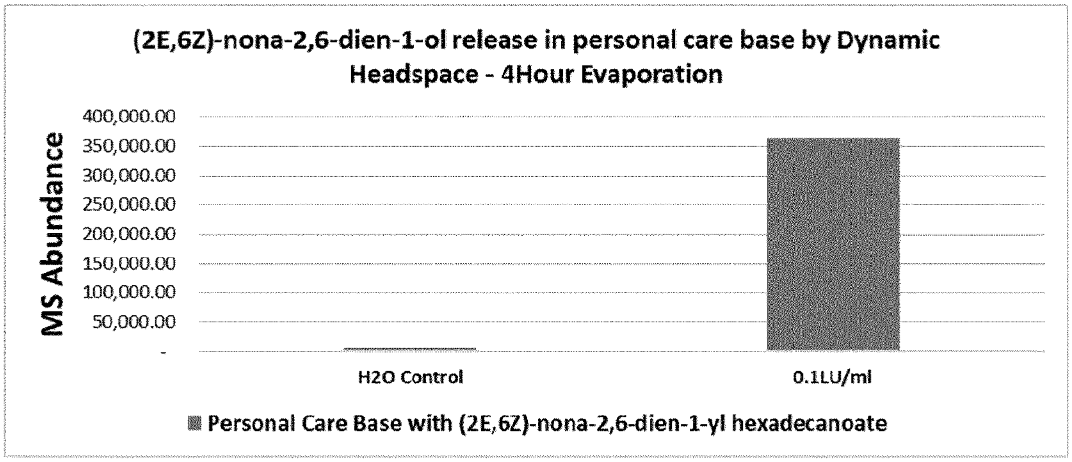
FIG. 5: Analysis of the abundance of (2E,6Z)-nona-2,6-dien-1-ol in headspace after 4 hours evaporation on a surface in a personal care base (in presence of physiologically relevant concentration of Hydrolase (0.1 LU/ml)).

The results of the released (2E,6Z)-nona-2,6-dien-1-ol from (2E,6Z)-nona-2,6-dien-1-yl hexadecanoate in personal care base with physiologically relevant concentration of Hydrolase (0.1 LU/ml) are shown in FIG. 5. In absence of hydrolase (water control) no release is observed.

Example 6

Paneling of Released Fragrance Alcohols on Glass Slides

Evaporation kinetics using 76 mm×51 mm glass slides was carried out. Prazitherm precision hotplate was pre-heated to 32 degrees Celsius for 30 minutes. Three glass slides were placed on the precision hotplate. Each glass slide is labeled with a unique code so that its identity is unknown to the panelists. Using a Gilson Microman M25 positive displacement pipette, ill of 0.1 LU lipase solution was dosed directly to the center of one of the glass slides. Then 20 μl of 1% (2E,6Z)-nona-2,6-dien-1-yl hexadecanoate was dosed very slowly to the lipase droplet. Once all the sample solution was applied onto the glass slide, the applied glass slide was evaporated on the precision hotplate for 4 hours at 32 degrees Celsius. Sample preparation for 1% (Z)-3-hexen-1-yl hexadecanoate solution and 1% 3,7-dimethyl-2,6-octa-dien-1-yl hexadecanoate solution were done the same way. Sample preparations for all three solutions were repeated for duplicates to replace each glass slide twice during the sensory panel period—the limit for a glass slide sample set (with 3 different glass slide samples) was 10 evaluations. At the 4-hour time interval, a spray bottle filled with deionized water was primed and then water was sprayed directly onto each glass slide once. One spray was enough to cover the glass slide. All glass slides were allowed to sit for 10 minutes before the sensory panel so the water was absorbed by the evaporated mixtures to represent humidity on skin. For evaluation, the panelist picks up the treated glass slides, smells the center and rates the intensity of each slide on an evaluation sheet.

Figure 6:
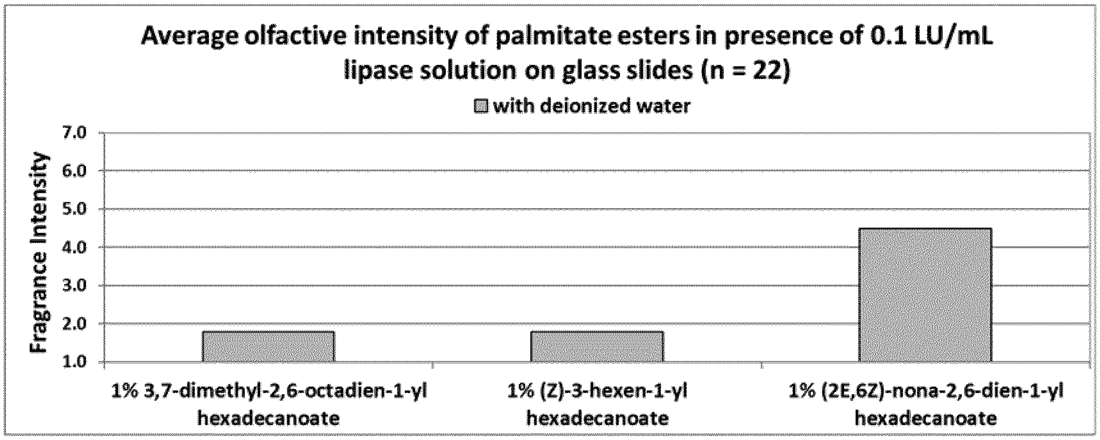
FIG. 6: Panel measuring the performance of 3,7-dimethyl-2,6-octadien-1-yl hexadecanoate, (Z)-3-hexen-1-yl hexadecanoate and (2E,6Z)-nona-2,6-dien-1-yl hexadecanoate on glass slide at 0.1 LU/ml after 4 hours.
Figure 7:
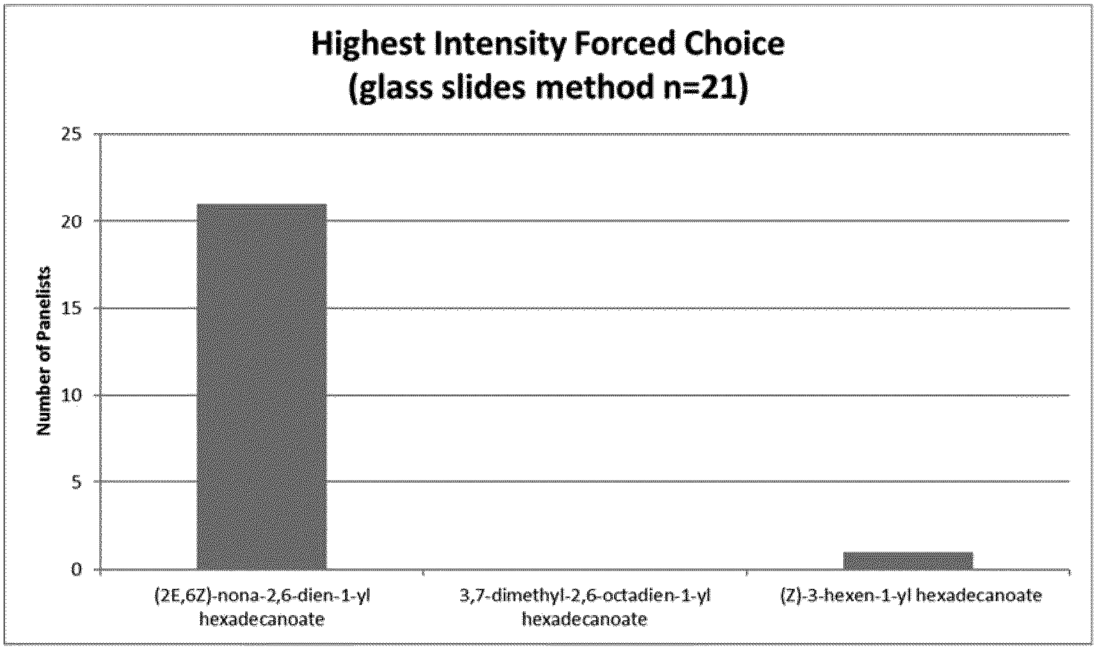
FIG. 7: Force Choice Sensory Validation of 3,7-dimethyl-2,6-octadien-1-yl hexadecanoate, (Z)-3-hexen-1-yl hexadecanoate and (2E,6Z)-nona-2,6-dien-1-yl hexadecanoate on glass slide at 0.1 LU/ml after 4 hours.

In one test, the panelists rated odor intensity on a scale of 1 to 7 for each glass slide evaluated under release by the hydrolase at time 4 hours. The results are shown in FIG. 6. The second approach was the so-called forced choice where panelists were forced to select the most intense out of the three hexanoate esters after release with the Hydrolase at 4 hours at 0.1 LU/ml. The results are shown in FIG. 7.

It was observed that (2E,6Z)-nona-2,6-dien-1-yl hexadecanoate was found to be significantly more intense than 3,7-dimethyl-2,6-octadien-1-yl hexadecanoate or (Z)-3-hexen-1-yl hexadecanoate.

If forced to choose, 20/21 panelists selected (2E,6Z)-nona-2,6-dien-1-yl hexadecanoate as the most intense sample. Although (Z)-3-hexen-1-yl hexadecanoate was observed to also release faster than 3,7-dimethyl-2,6-octadien-1-yl hexadecanoate it was not well perceived by the panelists. (2E,6Z)-nona-2,6-dien-1-yl hexadecanoate was the one providing the most intense impression.

Example 7

Performance of a Fine Fragrance Applied on Skin Comprising Compound of Formula (I)

TABLE 2

Fine Fragrance Formula.

| Ingredient | Parts |
|---|---|
| Ethyl 2-methylpentanoate | 5 |
| 2,6-dimethyl-5-heptenal | 0.5 |
| 2,4-dimethyl-3-cyclohexene-1-carbaldehyde | 5 |
| Methyl 2,2-dimethyl-6-methylidenecyclohexanecarboxylate | 4 |
| (E)-2-nonenal | 0.5 |
| 1-phenylethyl acetate | 50 |
| 2,6-dimethyl-7-octen-2-ol | 1200 |
| 2-(2-methyl-2-propanyl)cyclohexyl acetate | 350 |
| 3,7-dimethyl-1,6-nonadien-3-ol | 350 |
| Allyl (2/3-methylbutoxy)acetate | 100 |
| 3-(6,6-dimethyl-bicyclo[3.1.1]hept-2-en-2-yl)propanal | 3 |
| (E)-3-methyl-4-(2,6,6-trimethyl-2-cyclohexen-1-yl)-3-buten-2-one | 50 |
| (2E)-1-(2,6,6-trimethyl-2-cyclohexen-1-yl)-2-buten-1-one | 9 |
| Methyl 2-aminobenzoate | 1 |
| Allyl 3-cyclohexylpropanoate | 10 |
| 1-(3,3/5,5-dimethyl-1-cyclohexen-1-yl)-4-penten-1-one | 10 |
| (2E)-1-(2,6,6-trimethyl-1,3-cyclohexadien-1-yl)-2-buten-1-one | 3 |
| 1,2,3,5,6,7-hexahydro-1,1,2,3,3-pentamethyl-4-indenone | 100 |
| (4E)-3,3-dimethyl-5-[(1R)-2,2,3-trimethyl-3-cyclopenten-1-yl]-4-penten-2-ol | 50 |
| 2,6,10-trimethyl-9-undecenal | 10 |
| 1-(octahydro-2,3,8,8-tetramethyl-2-naphtalenyl)-1-ethanone | 1000 |
| 2-methyl-3-[4-(2-methyl-2-propanyl)phenyl]propanal | 150 |
| 7-isopropyl-2h,4h-1,5-benzodioxepin-3-one | 1 |
| 8(9)-methoxy-tricyclo[5.2.1.0.(2,6)]decane-3(4)-carbaldehyde | 20 |
| 3-(4-tert-butylphenyl)propanal | 10 |
| (8R)-8,12-epoxy-13,14,15,16-tetranorlabdane | 200 |
| (Ethoxymethoxy)cyclododecane | 300 |
| 2-ethyl-4-(2,2,3-trimethyl-3-cyclopenten-1-yl)-2-buten-1-ol | 100 |
| (1S,1'R)-[1-(3',3'-Dimethyl-1'-cyclohexyl)ethoxycarbonyl]methyl propanoate | 100 |
| Methyl 2-(3-oxo-2-pentylcyclopentyl)acetate | 550 |
| Hexyl 2-hydroxybenzoate | 100 |
| 3-Methyl-5-cyclopentadecen-1-one | 10 |
| Methyl 2,4-dihydroxy-3,6-dimethylbenzoate | 50 |
| 4-hydroxy-3-methoxybenzaldehyde | 110 |

TABLE 2-continued

Fine Fragrance Formula.

| Ingredient | Parts |
|---|---|
| 1-(octahydro-2,3,8,8-tetrame-2-naphthalenyl)-1-ethanone | 1300 |
| 4,6,6,7,8,8-hexamethyl-1,3,4,6,7,8-hexahydrocyclopenta[g]isochromene | 1603 |
| 1-(3,5,5,6,8,8-hexamethyl-5,6,7,8-tetrahydro-2-naphthalenyl)ethanone | 200 |
| Trans-1-(2,2,6-trimethyl-1-cyclohexyl)-3-hexanol | 60 |
| (2E)-2-benzylideneoctanal | 500 |
| 2-chromenone | 300 |
| 5,5,9,13-tetramethyl-14,16-dioxatetracyclo[11.2.1.0$^{1,10}$.0$^{4,9}$]hexadecane | 30 |
| (1R,3S,7R,8R,10S,13R)-5,5,7,9,9,13-hexamethyl-4,6-dioxatetracyclo[6.5.1.0(1,10).0(3,7)]tetradecane | 40 |
| Amber | 30 |
| Bergamot oil | 500 |
| Cardamom oil | 30 |
| Cedarwood oil | 200 |
| Cypress oil | 100 |
| Dipropylene glycol | 43 |
| Elemi oil | 50 |
| Guaiac wood oil | 100 |
| Lavandin oil | 150 |
| Vetiver oil | 100 |
| | 10348 |

To this fine fragrance formula corresponding to fragrance A was added 0.7 part of (2E,6Z)-nona-2,6-dien-1-yl hexadecanoate corresponding to fragrance B or was added 2 part of (2E,6Z)-nona-2,6-dien-1-yl hexadecanoate corresponding to fragrance C. Each fragrance, A to C, was dosed at 18% by weight in ethanol/water (95:5). The fragrance solution was dosed with 3 pump sprays (~240 ul) on the forearms of 2 individuals. Fragrance was worn for 6 hours avoiding contact to clothing. Evaluation was done after 6 hours drydown and evaluated by 3 trained and 3 expert (perfumer) evaluators for intensity and freshness.

All panelists found that fragrance C is the most intense and fresh and that fragrance A is the weakest in intensity and freshness.

Example 8

Preparation of a Perfume Oil

A non-limiting example of a typical perfume oil is prepared by admixing the following perfuming co-ingredients:

| Ingredients | weight-% |
|---|---|
| Ethyl 2-methylbutanoate | 0.16 |
| Hexyl acetate | 0.37 |
| Limonene | 1.67 |
| 2,6-Dimethyl-7-octen-2-ol | 0.94 |
| 2-Phenylethanol | 2.15 |
| Linalool | 0.73 |
| (2RS,4SR/4RS)-4-Methyl-2-(2-methyl-1-propen-1-yl)tetrahydro-2H-pyran | 0.30 |
| Ethyl 2-methyl-1,3-dioxolane-2-acetate | 0.32 |
| Benzyl acetate | 2.46 |
| Allyl heptanoate | 0.38 |
| alpha-Terpineol | 0.88 |
| 3,7-Dimethyl-6-octen-1-ol | 0.55 |
| 4-Methoxybenzaldehyde | 1.00 |
| (E)-4-Methyl-3-decen-5-ol | 0.37 |
| [cis/trans-4-(2-Propanyl)cyclohexyl]methanol | 0.47 |
| 1-Methoxy-4-[(1E)-1-propen-1-yl]benzene | 0.15 |
| (1RS,2RS/2SR)-2-(2-Methyl-2-propanyl)cyclohexyl acetate | 1.95 |
| 1,1-Dimethyl-2-phenylethyl acetate | 0.95 |

-continued

| Ingredients | weight-% |
|---|---|
| Tricyclo[5.2.1.0$^{2,}$~]dec-3/4-en-8-yl acetate | 3.34 |
| Allyl 3-cyclohexylpropanoate | 0.26 |
| 3-(4-Isopropylphenyl)-2-methylpropanal | 8.18 |
| (3E)-3-Methyl-4-(2,6,6-trimethyl-2-cyclohexen-1-yl)-3-buten-2-one and (1E)-1-(2,6,6-trimethyl-2-cyclohexen-1-yl)-1-penten-3-one | 1.13 |
| 2-Phenoxyethyl 2-methylpropanoate | 5.38 |
| Tricyclo[5.2.1.0(2,6)]dec-3/4-en-8-yl propanoate | 2.32 |
| 5-Heptyldihydro-2(3H)-furanone | 2.30 |
| 2/3-Methylbutyl salicylate | 1.42 |
| (3Z)-3-Hexen-1-yl salicylate | 0.31 |
| 1-(2,3,8,8-Tetramethyl-1,3,4,5,6,7-hexahydronaphthalen-2-yl)ethanone | 16.03 |
| Hexyl 2-hydroxybenzoate | 5.04 |
| (2E)-2-Benzylideneoctanal | 21.22 |
| (−)-(3aR,5aS,9aS,9bR)-3a,6,6,9a-Tetramethyldodecahydronaphtho[2,1-b]furan | 0.27 |
| Habanolide ® | 4.78 |
| Exaltolide ® | 3.82 |
| Benzyl 2-hydroxybenzoate | 3.01 |
| Dipropylene glycol | 5.39 |
| Total: | 100 |

Example 9

Preparation of Anhydrous Antiperspirant Spray Formulations Comprising a Compound of Formula (I)

A typical unperfumed anhydrous antiperspirant spray formulation is listed in Table 3. The anhydrous antiperspirant spray formulation is prepared by using a high speed stirrer. Silica and Quaternium-18-hectorite are added to the mixture of isopropyl myristate and cyclomethicone. Once completely swollen, aluminium chlorohydrate is added portion-wise under stirring until the mixture becomes homogeneous and without lumps.

TABLE 3

Composition of a typical unperfumed anhydrous antiperspirant spray.

| Ingredients | Amount [wt %] |
|---|---|
| Cyclomethicone (1) | 53.51 |
| Isopropyl myristate | 9.04 |
| Silica (2) | 1.03 |
| Quaternium-18-hectorite (3) | 3.36 |
| Aluminium chlorohydrate (4) | 33.06 |

(1) Dow Corning ® 345 Fluid; origin: Dow Corning
(2) Aerosil ® 200; origin: Evonik
(3) Bentone ® 38; origin: Elementis Specialities
(4) Micro Dry Ultrafine; origin: Reheis The perfumed formulation is then obtained by adding the perfume oil of example 8 (0.85% by weight relative to the total weight of the antiperspirant spray formulation) and at least one of the compounds of formula (I) (0.15% by weight relative to the total weight of the antiperspirant spray formulation) into the unperfumed antiperspirant spray formulation of Table 2.

The aerosol cans are filled with 25% Suspension of the suspension and 75% of Propane/Butane (2.5 bar).

Example 10

Preparation of Deodorant Spray Emulsion Formulations Comprising a Compound of Formula A typical deodorant spray emulsion formulation is prepared by mixing and dissolving all the ingredients according to the sequence of Table 4. Then a perfume oil as reported in Example 8 (1.35% by weight relative to the total weight of the deodorant spray formulation) and at least one compounds of formula (I) (0.10 to 0.20% by weight relative to the total weight of the deodorant spray formulation) are added under gentle shaking. Then aerosol cans are filled, and the propellant is crimped and added. Aerosol filling: 40% active solution 60% propane/butane (2.5 bar).

TABLE 4

Composition of a typical unperfumed deodorant spray formulation.

| Ingredients | Amount [wt %] |
|---|---|
| Ethanol (95%) | 90.65 |
| Triclosan (1) | 0.26 |
| Isopropyl myristate | 9.09 |

(1) Irgasan ® DP 300; origin: BASF

Example 11

Preparation of Deodorant Stick Formulations Comprising a Compound of Formula (I)

A typical unperfumed deodorant stick formulation is listed in Table 5. The deodorant stick formulation is obtained by weighing all the components of Part A and heating to 70-75° C. Ceteareth-25 is added once the other Part A ingredients are mixed and heated. Once the Ceteareth-25 is dissolved, stearic acid is added. Part B is prepared by dissolving Triclosan in 1,2-propylene glycol. Evaporated water is compensated. Then, slowly, under mixing, Part B is poured into Part A.

TABLE 5

Composition of a typical unperfumed deodorant stick formulation.

| Phase | Ingredients | Amount [wt %] |
|---|---|---|
| A | Stearic acid | 5.05 |
| | 1,2-Propylene glycol | 41.87 |
| | Sodium hydroxide (20% aqueous solution) | 4.24 |
| | Water | 30.30 |
| | Tetrasodium EDTA (1) | 0.10 |
| | Ceteareth-25 (2) | 1.52 |
| | PPG-3 Myristyl ether (3) | 1.52 |
| B | 1,2-Propylene glycol | 15.14 |
| | Triclosan (4) | 0.25 |

(1) Edeta ® B Power; origin: BASF
(2) Cremophor ® A25; origin: BASF
(3) Tegosoft ® APM; origin: Evonik
(4) Irgasan ® DP 300; origin: BASF The perfumed deodorant stick formulation is then obtained by adding the perfume oil of Example 8 (0.85% by weight relative to the total weight of the deodorant stick formulation) and at least one compounds of formula (I) (0.10 to 0.20% by weight relative to the total weight of the deodorant stick formulation) under gentle shaking. To stock, a plastic bag is put into the bucket to be sealed after cooling. Moulds were filled at about 70° C.

Example 12

Preparation of Deodorant Roll-on Formulations Comprising a Compound of Formula (I)

A typical unperfumed deodorant roll-on formulation is listed in Table 6. Part A is prepared by sprinkling little-by-little the hydroxyethylcellulose into the water, whilst rapidly stirring with a turbine until the hydroxyethylcellulose is entirely swollen giving a limpid gel. Part B is slowly poured into Part A, whilst continuing stirring until the entire mixture is homogeneous. Then Part C is added.

TABLE 6

Composition of a typical unperfumed deodorant roll-on formulation.

| Phase | Ingredients | Amount [wt %] |
|---|---|---|
| A | Water | 50.51 |
| | Hydroxyethylcellulose [(1)] | 0.71 |
| B | Ethanol (95%) | 40.40 |
| | 1,2-Propylene glycol | 5.05 |
| | Triclosan [(2)] | 0.30 |
| C | PEG-40 hydrogenated castor oil [(3)] | 3.03 |

[(1)] Natrosol ® 250 H; origin: Ashland
[(2)] Irgasan ® DP 300; origin: BASF
[(3)] Cremophor ® RH 40; origin: BASF The perfumed deodorant roll-on formulation is then obtained by adding the perfume oil of Example 8 (0.85% by weight relative to the total weight of the deodorant stick formulation) and at least one compounds of formula (I) (0.10-0.20% by weight relative to the total weight of the deodorant stick formulation) under gentle shaking.

Example 13

Preparation of Day Cream Base O/W Emulsions Comprising a Compound of Formula (I)

A typical day cream base O/W emulsion formulation comprising a compound of formula (I) is listed in Table 7. Phases A and B are heated separately to 70-75° C., then Phase A is added to Phase B and vacuum is applied. The mixture is stirred and cooled to 55° C. for 15 min. After cooling to room temperature, phenoxyethanol (and) piroctone olamine (Part C) are added when a temperature of 45° C. is reached. The mixture is stirred for 5 min before sodium carbomer (Part D), a perfume oil and at least one compounds of formula (I) (Part E) are added. The mixture is stirred for 3 min, then the stirring was stopped for 15 min. When the temperature of the mixture reaches 30° C., the stirring is resumed for another 15 min until the cream becomes homogeneous, glossy and without lumps. If necessary the pH is adjusted to 6.70-7.20 with Glydant®, Phenoni® p or Nipaguard® P05 or to 6.30-7.00 with Nikkoguard®.

TABLE 7

Composition of a typical day cream base O/W emulsion.

| Phase | Ingredients | Amount [wt %] |
|---|---|---|
| A | Steareth-2 (and) PEG-8 Distearate[(1)] | 5.0 |
| | Cetyl alcohol | 0.5 |
| | Ceteth-20 (and) glyceryl stearate (and) PEG-6 stearate (and) Steareth-20 [(2)] | 4.0 |
| | Squalan [(3)] | 1.0 |
| | Paraffin oil [(4)] | 2.0 |
| | Petrolatum [(5)] | 5.5 |
| B | Deionized water | 75.9 |
| | Propylene glycol | 5.0 |
| C | Phenoxyethanol (and) Piroctone olamine [(6)] | 0.6 |
| D | Sodium carbomer [(7)] | 0.2 |
| E | Perfume oil of Example 8 | 0.15 |
| | Compound of formula (I) | 0.15 |

[(1)]Arlacel ® 985; origin: Croda
[(2)] Tefose ® 2561; origin: Gattefossé
[(3)] Biolip P 90; origin: Gattefossé
[(4)] Mineral oil 30-40 CPS
[(5)] Petroleum jelly
[(6)] Nipaguard ® PO 5; origin: Clariant
[(7)] PNC 400

Example 14

Preparation of a Body Spray Comprising a Compound of Formula (I)

A typical body spray is prepared by mixing and dissolving all the ingredients according to the sequence of Table 8. Then aerosol cans are filled, and the propellant is crimped and added. Aerosol filling: 40% active solution 60% propane/butane (2.5 bar).

TABLE 8

Composition of a typical unperfumed deodorant spray formulation.

| Ingredients | Amount [wt %] |
|---|---|
| Ethanol (95%) | up to 100 |
| Perfume oil of Example 8 | 1.5-2.5 |
| Compound of formula (I) | 0.1-1 |
| Propellant | 40-50 |

Example 15

Preparation of Rinse-Off Hair Conditioner Formulations Comprising Compound of Formula (I)

A typical unperfumed rinse-off hair conditioner formulation is listed in Table 9. The unperfumed rinse-off hair conditioner formulation is prepared by mixing the ingredients of Phase A until an uniform mixture was obtained. Tylose® is allowed to completely dissolve. Then the mixture is heated to 70-75° C. The ingredients of Phase B are combined and melted at 70-75° C. Then the ingredients of Phase B are added to Phase A with good agitation, and the mixing is continued until that the mixture has a temperature of 60° C. Then, the ingredients of Phase C are added while agitating and keeping mixing until the mixture cooled to 40° C. The pH is adjusted with a citric acid solution to 3.5-4.0.

TABLE 9

Composition of a typical rinse-off hair conditioner formulation.

| Phase | Ingredients | Amount [wt %] |
|---|---|---|
| A | Deionized water | 81.8 |
| | Behentrimonium chloride [(1)] | 2.5 |
| | Hydroxyethylcellulose [(2)] | 1.5 |
| B | Cetearyl alcohol [(3)] | 4.0 |
| | Glyceryl stearate (and) PEG-100 stearate [(4)] | 2.0 |
| | Behentrimonium metho-sulfate (and) cetyl alcohol (and) butylene glycol [(5)] | 4.0 |
| | Ethoxy (20) stearyl alcohol [(6)] | 1.0 |
| C | Amodimethicone (and) Trideceth-12 (and) Cetrimonium chloride [(7)] | 3.0 |
| | Chlorhexidine digluconate (20% aqueous solution) [(8)] | 0.2 |
| D | Citric acid (10% aqueous solution tol pH 3.5-4.0) | q.s. |

[(1)] Genamin ® KDMP; origin: Clariant
[(2)] Tylose ® H10 Y G4; origin: Shin Etsu
[(3)] Lanette ® O; origin: BASF
[(4)] Arlacel ® 165; origin: Croda
[(5)] Incroquat ® Behenyl TMS-50-PA- (MH); origin: Croda
[(6)] Brij ® S20; origin: Croda
[(7)] Xiameter ® MEM-949; origin: Dow Corning
[(8)] Origin: Alfa Aesar A perfumed rinse-off hair conditioner formulation is then obtained by adding, under gentle shaking, a perfume oil as reported in Example 8 (0.2 to 1.0% by weight relative to the total weight of the unperfumed conditioner formulation) and at least one of the compounds of formula (I) (0.05 to 0.5% by weight relative to the total weight of the unperfumed conditioner formulation) into the unperfumed rinse-off hair conditioner formulation listed in Table 8.

The invention claimed is:

1. A perfumed consumer product comprising a) a perfume oil comprising at least one compound of formula (I)

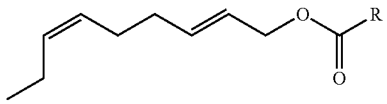

(I)

wherein R represents a linear or branched, saturated or unsaturated C7-24 alkyl group; and b) optionally, a personal care active base.

2. The perfumed consumer product according to claim 1, wherein R is a linear, saturated or unsaturated C9-21 alkyl group.

3. The perfumed consumer product according to claim 1, wherein R is a linear saturated C10-18 alkyl group.

4. The perfumed consumer product according to claim 1, wherein R is a linear saturated C11-16 alkyl group.

5. The perfumed consumer product according to claim 1, wherein the compound of formula (I) is (2E,6Z)-nona-2,6-dien-1-yl hexadecanoate, (2E,6Z)-nona-2,6-dien-1-yl tetradecanoate and (2E,6Z)-nona-2,6-dien-1-yl dodecanoate.

6. The perfumed consumer product according to claim 1, wherein the perfumed consumer product is in a form of a leave-on consumer product.

7. The perfumed consumer product according to claim 6, wherein the leave-on consumer product is a fine perfume, an eau de toilette, an eau de parfum, a cologne or a shave or after-shave lotion.

8. The perfumed consumer product according to claim 7, wherein the fine perfume, the eau de toilette, the eau de parfum, the cologne or the shave or after-shave lotion comprise a) 0.0001% to 5% w/w, of at least one compound of formula (I)

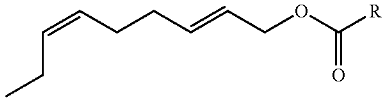

(I)

wherein R represents a linear or branched, saturated or unsaturated C7-24 alkyl group;

b) 20% to 90% w/w of a perfumery carrier wherein the perfumery carrier is ethanol;

c) 0.3% to 30% w/w of at least one perfumery co-ingredient; and d) optionally at least one perfumery adjuvant;

the percentage being relative to the total weight of the perfumed consumer product.

9. The perfumed leave-on consumer product according to claim 6, wherein it is in the form of a body spray or body splash.

10. The perfumed leave-on consumer product according to claim 6, wherein it is in the form of a skin care product.

11. The perfumed leave-on consumer product according to claim 10, wherein the skin care product is a face cream, a face lotion, a shaving product, a body and/or hand product, a skin firming product, a depilatory, a talcum powder, a foot care cream or lotion, a baby wipe, a cleansing wipe, a moisturizer wipe, a sun-protection product, an after-sun lotion, or a self-tanning product.

12. The perfumed leave-on consumer product according to claim 6, wherein it is in the form of a deodorant or antiperspirant product.

13. The perfumed leave-on consumer product according to claim 12, wherein the deodorant or antiperspirant product is a body deodorant spray, a roll-on deodorant, a deodorant stick, a deodorant cream, an antiperspirant spray, an antiperspirant stick, a roll-on antiperspirant liquid or an antiperspirant cream.

14. The perfumed leave-on consumer product according to claim 6, wherein it is in the form of a leave-on hair care product.

15. The perfumed consumer product according to claim 5, wherein the perfumed consumer product is in a form of a leave-on consumer product.

16. The perfumed leave-on consumer product according to claim 15, wherein the leave-on consumer product is a fine perfume, an eau de toilette, an eau de parfum, a cologne, a shave or after-shave lotion, a body spray or body splash, a skin care product, a deodorant or antiperspirant product, or a leave-on hair care product.

17. The perfumed consumer product according to claim 8, wherein the fine perfume, the eau de toilette, the eau de parfum, the cologne or the shave or after-shave lotion comprise a) 0.01% to 1% w/w of at least one compound of formula (I);

b) 40% to 90% w/w of a perfumery carrier wherein the perfumery carrier is ethanol;

c) 1% to 15% w/w of at least one perfumery co-ingredient; and d) optionally at least one perfumery adjuvant;

the percentage being relative to the total weight of the perfumed consumer product.

18. A method of imparting a long-lasting or substantive green odor to a surface, the method comprising adding at least one compound of formula (I) as defined in claim 1 to a perfuming composition or perfumed consumer product and applying the perfuming composition or perfumed consumer product to the corresponding targeted surface.

19. The method according to claim 18, wherein the compound of formula (I) is (2E,6Z)-nona-2,6-dien-1-yl hexadecanoate, (2E,6Z)-nona-2,6-dien-1-yl tetradecanoate and (2E,6Z)-nona-2,6-dien-1-yl dodecanoate.

* * * * *